(12) United States Patent
Franano et al.

(10) Patent No.: US 11,090,176 B2
(45) Date of Patent: Aug. 17, 2021

(54) DETACHABLE METAL BALLOON DELIVERY DEVICE AND METHOD

(75) Inventors: F. Nicholas Franano, Olathe, KS (US); Katherine J. Stephenson, Los Gatos, CA (US)

(73) Assignee: Artio Medical, Inc., Prairie Village, KS (US)

( * ) Notice: Subject to any disclaimer, the term of this patent is extended or adjusted under 35 U.S.C. 154(b) by 0 days.

(21) Appl. No.: 13/980,278

(22) PCT Filed: Jan. 17, 2012

(86) PCT No.: PCT/US2012/021620
§ 371 (c)(1),
(2), (4) Date: Sep. 26, 2013

(87) PCT Pub. No.: WO2012/099909
PCT Pub. Date: Jul. 26, 2012

(65) Prior Publication Data
US 2014/0012307 A1    Jan. 9, 2014

Related U.S. Application Data

(60) Provisional application No. 61/433,305, filed on Jan. 17, 2011.

(51) Int. Cl.
*A61F 2/958* (2013.01)
*A61B 17/12* (2006.01)
(Continued)

(52) U.S. Cl.
CPC ........ *A61F 2/958* (2013.01); *A61B 17/12031* (2013.01); *A61B 17/12109* (2013.01);
(Continued)

(58) Field of Classification Search
CPC ............ A61F 2/958; A61M 2025/1086; A61B 17/12136; A61B 17/12113; A61B 17/12022
(Continued)

(56) References Cited

U.S. PATENT DOCUMENTS

| 3,794,268 A | 2/1974 | McNeill |
| 4,311,146 A | 1/1982 | Wonder |

(Continued)

FOREIGN PATENT DOCUMENTS

| CN | 1342056 A | 3/2002 |
| CN | 1813638 A | 8/2006 |

(Continued)

OTHER PUBLICATIONS

European Extended Search Report; Application No. 12736799.3 dated Oct. 2, 2014 (12 pages).
(Continued)

*Primary Examiner* — Majid Jamialahmadi
(74) *Attorney, Agent, or Firm* — Polsinelli PC

(57) ABSTRACT

A medical device comprising a compressed, inflatable, detachable single-lobed metal balloon attached to a catheter and methods of use for occluding blood vessels or treating vascular aneurysms are disclosed. The balloon can be made with ductile metals such as gold, platinum, or silver so that the balloon will conform to the shape of the void space during inflation and so that the balloon can be subsequently shaped by the application of an external force. The balloon can be configured such that it can be detached from the catheter by physical means or by electrolysis. The surface of the balloon can be configured to promote the growth of tissue into the wall of the balloon and to release drugs or pharmacologically active molecules, so that vessel occlusion or the sealing of an aneurysm will be maintained over time.

64 Claims, 13 Drawing Sheets

(51) Int. Cl.
*A61F 2/06* (2013.01)
*A61M 25/10* (2013.01)
*A61B 90/00* (2016.01)
*A61B 17/00* (2006.01)

(52) U.S. Cl.
CPC .. *A61B 17/12131* (2013.01); *A61B 17/12136* (2013.01); *A61F 2/06* (2013.01); *A61M 25/1029* (2013.01); A61B 2017/00526 (2013.01); A61B 2017/00893 (2013.01); A61B 2017/12054 (2013.01); A61B 2017/12059 (2013.01); A61B 2017/12063 (2013.01); A61B 2017/12068 (2013.01); A61B 2090/037 (2016.02); Y10T 29/49826 (2015.01)

(58) Field of Classification Search
USPC .................................. 606/192–195
See application file for complete search history.

(56) References Cited

U.S. PATENT DOCUMENTS

| | | | |
|---|---|---|---|
| 4,341,218 A | 7/1982 | Ü | |
| 4,364,392 A | 12/1982 | Strother et al. | |
| 4,395,806 A | 8/1983 | Wonder et al. | |
| 4,402,319 A | 9/1983 | Handa et al. | |
| 4,416,028 A | 11/1983 | Eriksson et al. | |
| 4,471,779 A | 9/1984 | Antoshkiw et al. | |
| 4,517,979 A | 5/1985 | Pecenka | |
| 4,638,803 A * | 1/1987 | Rand | A61B 17/12136 604/175 |
| 4,770,067 A | 9/1988 | Liu et al. | |
| 4,819,637 A | 4/1989 | Dormandy, Jr. et al. | |
| 5,041,090 A * | 8/1991 | Scheglov | A61B 17/12022 604/101.02 |
| 5,167,627 A * | 12/1992 | Clegg | A61B 17/3415 604/103.03 |
| 5,181,921 A | 1/1993 | Makita et al. | |
| 5,222,970 A * | 6/1993 | Reeves | A61B 17/12109 604/164.05 |
| 5,250,059 A | 10/1993 | Andreas et al. | |
| 5,282,847 A | 2/1994 | Trescony et al. | |
| 5,327,885 A | 7/1994 | Griffith | |
| 5,344,401 A * | 9/1994 | Radisch | A61M 25/1027 604/103.06 |
| 5,354,295 A | 10/1994 | Guglielmi et al. | |
| 5,370,691 A | 12/1994 | Samson | |
| 5,382,261 A * | 1/1995 | Palmaz | A61B 17/12022 604/907 |
| 5,522,836 A | 6/1996 | Palermo | |
| 5,527,337 A * | 6/1996 | Stack | A61F 2/90 606/198 |
| 5,609,606 A | 3/1997 | O'Boyle | |
| 5,769,817 A * | 6/1998 | Burgmeier | A61L 29/04 604/103.06 |
| 5,833,671 A | 11/1998 | Macoviak et al. | |
| 5,902,308 A | 5/1999 | Murphy | |
| 5,980,530 A * | 11/1999 | Willard | A61F 2/958 606/195 |
| 6,022,359 A | 2/2000 | Frantzen | |
| 6,063,070 A | 5/2000 | Eder | |
| 6,096,021 A * | 8/2000 | Helm | A61B 17/12113 604/103.01 |
| 6,146,372 A | 11/2000 | Leschinsky et al. | |
| 6,156,005 A | 12/2000 | Theron | |
| 6,186,978 B1 | 2/2001 | Samson et al. | |
| 6,187,034 B1 | 2/2001 | Frantzen | |
| 6,293,960 B1 | 9/2001 | Ken | |
| 6,293,968 B1 | 9/2001 | Taheri | |
| 6,312,405 B1 | 11/2001 | Meyer et al. | |
| 6,344,041 B1 | 2/2002 | Kupiecki et al. | |
| 6,346,117 B1 | 2/2002 | Greenhalgh | |
| 6,375,668 B1 * | 4/2002 | Gifford | A61B 17/12022 606/200 |
| 6,395,008 B1 * | 5/2002 | Ellis | A61F 2/958 606/108 |
| 6,409,754 B1 | 6/2002 | Smith et al. | |
| 6,425,893 B1 | 7/2002 | Guglielmi | |
| 6,454,780 B1 | 9/2002 | Wallace | |
| 6,463,317 B1 * | 10/2002 | Kucharczyk | A61B 5/02014 600/411 |
| 6,676,667 B2 | 1/2004 | Mareiro et al. | |
| 6,706,064 B1 | 3/2004 | Anson | |
| 6,733,513 B2 * | 5/2004 | Boyle | A61F 2/82 606/192 |
| 6,976,950 B2 | 12/2005 | Connors et al. | |
| 6,976,951 B2 | 12/2005 | Connors et al. | |
| 7,252,677 B2 * | 8/2007 | Burwell | A61N 5/0601 606/13 |
| 7,329,236 B2 | 2/2008 | Kesten et al. | |
| 7,410,482 B2 * | 8/2008 | Murphy | A61B 17/12022 606/1 |
| 7,527,622 B2 * | 5/2009 | Lane | A61B 18/02 604/101.01 |
| 7,632,291 B2 | 12/2009 | Stephens et al. | |
| 7,632,301 B2 | 12/2009 | Alt | |
| 7,713,297 B2 | 5/2010 | Alt | |
| 7,955,246 B2 | 6/2011 | Lubock et al. | |
| 8,007,674 B2 | 8/2011 | Johnson | |
| 8,016,853 B2 | 9/2011 | Griffen et al. | |
| 8,333,798 B2 | 12/2012 | Gandhi et al. | |
| 8,372,114 B2 | 2/2013 | Hines | |
| 8,574,146 B2 | 11/2013 | Gillespie, Jr. et al. | |
| 8,668,717 B2 | 3/2014 | Hines | |
| 9,283,100 B2 | 3/2016 | Wang et al. | |
| 9,572,697 B2 | 2/2017 | Franano et al. | |
| 9,572,698 B2 | 2/2017 | Franano et al. | |
| 2002/0016624 A1 | 2/2002 | Patterson et al. | |
| 2002/0026210 A1 | 2/2002 | Abdel-Gawwad | |
| 2002/0029035 A1 | 3/2002 | Lee et al. | |
| 2002/0052638 A1 | 5/2002 | Zadno-Azizi | |
| 2002/0052639 A1 | 5/2002 | Fischell et al. | |
| 2002/0082638 A1 * | 6/2002 | Porter | A61B 17/12113 606/195 |
| 2002/0143383 A1 | 10/2002 | Parodi | |
| 2002/0165572 A1 | 11/2002 | Saadat | |
| 2002/0169473 A1 | 11/2002 | Septka et al. | |
| 2003/0028210 A1 | 2/2003 | Boyle et al. | |
| 2003/0074039 A1 | 4/2003 | Puskas | |
| 2003/0083732 A1 | 5/2003 | Stinson | |
| 2003/0135265 A1 | 7/2003 | Stinson | |
| 2003/0171739 A1 | 9/2003 | Murphy et al. | |
| 2003/0187492 A1 | 10/2003 | McHale | |
| 2003/0212419 A1 | 11/2003 | West | |
| 2003/0220666 A1 * | 11/2003 | Mirigian | A61B 17/12022 606/200 |
| 2003/0236494 A1 * | 12/2003 | Seward | A61M 25/007 604/97.01 |
| 2004/0019322 A1 | 1/2004 | Hoffmann | |
| 2004/0093014 A1 | 5/2004 | Ho et al. | |
| 2004/0138733 A1 | 7/2004 | Weber et al. | |
| 2004/0193177 A1 * | 9/2004 | Houghton | A61F 2/958 606/108 |
| 2004/0220610 A1 | 11/2004 | Kreidler et al. | |
| 2004/0236278 A1 | 11/2004 | Herweck et al. | |
| 2004/0243119 A1 | 12/2004 | Lane et al. | |
| 2004/0254625 A1 * | 12/2004 | Stephens | A61B 17/12022 623/1.1 |
| 2005/0033408 A1 | 2/2005 | Jones et al. | |
| 2005/0090888 A1 | 4/2005 | Hines et al. | |
| 2005/0136090 A1 | 6/2005 | Falotico et al. | |
| 2005/0171593 A1 | 8/2005 | Whirley et al. | |
| 2006/0015169 A1 | 1/2006 | Letort | |
| 2006/0079923 A1 | 4/2006 | Chhabra et al. | |
| 2006/0085070 A1 | 4/2006 | Kim | |
| 2006/0135947 A1 | 6/2006 | Soltesz et al. | |
| 2006/0155296 A1 | 7/2006 | Richter | |
| 2006/0155364 A1 | 7/2006 | Holloway et al. | |
| 2006/0155367 A1 * | 7/2006 | Hines | A61F 2/844 623/1.28 |
| 2006/0200191 A1 | 9/2006 | Zadno-Azizi | |
| 2006/0206199 A1 | 9/2006 | Churchwell et al. | |

(56) References Cited

U.S. PATENT DOCUMENTS

| | | | |
|---|---|---|---|
| 2006/0224229 A1* | 10/2006 | Goto | A61F 2/91 623/1.15 |
| 2007/0032854 A1 | 2/2007 | Schmid et al. | |
| 2007/0067009 A1 | 3/2007 | Gandhi et al. | |
| 2007/0112370 A1 | 5/2007 | Andrews et al. | |
| 2007/0129746 A1 | 6/2007 | Mische | |
| 2007/0150041 A1* | 6/2007 | Evans | A61B 17/12118 623/1.11 |
| 2007/0239191 A1 | 10/2007 | Ramzipoor | |
| 2007/0244431 A1 | 10/2007 | Limon | |
| 2007/0265656 A1 | 11/2007 | Amplatz et al. | |
| 2007/0267780 A1* | 11/2007 | Schewe | A61M 25/1029 264/299 |
| 2007/0288083 A1* | 12/2007 | Hines | A61B 17/12022 623/1.15 |
| 2007/0299422 A1 | 12/2007 | Inganas et al. | |
| 2007/0299460 A9 | 12/2007 | Boucher et al. | |
| 2008/0140177 A1 | 6/2008 | Hines | |
| 2008/0188825 A1 | 8/2008 | Atanasoska et al. | |
| 2008/0188923 A1 | 8/2008 | Chu | |
| 2008/0195112 A1 | 8/2008 | Liu et al. | |
| 2008/0281350 A1 | 11/2008 | Sepetka et al. | |
| 2008/0294205 A1 | 11/2008 | Greenhalgh et al. | |
| 2009/0062726 A1* | 3/2009 | Ford | A61B 17/12022 604/57 |
| 2009/0088829 A1 | 4/2009 | Wang et al. | |
| 2009/0287297 A1 | 11/2009 | Cox | |
| 2009/0297582 A1 | 12/2009 | Meyer et al. | |
| 2009/0299327 A1 | 12/2009 | Tilson et al. | |
| 2010/0096320 A1 | 4/2010 | Opperman | |
| 2010/0114299 A1 | 5/2010 | Ben Muvhar et al. | |
| 2010/0160949 A1 | 6/2010 | Takuma | |
| 2010/0174353 A1 | 7/2010 | Kantor | |
| 2010/0198336 A1 | 8/2010 | Weber et al. | |
| 2010/0222803 A1 | 9/2010 | Seifert et al. | |
| 2010/0241178 A1 | 9/2010 | Tilson et al. | |
| 2010/0268260 A1 | 10/2010 | Riina et al. | |
| 2010/0312179 A1* | 12/2010 | Nikolchev | A61B 17/025 604/96.01 |
| 2010/0324649 A1 | 12/2010 | Mattsson et al. | |
| 2011/0046658 A1 | 2/2011 | Connor et al. | |
| 2011/0190776 A1 | 8/2011 | Palmaz | |
| 2011/0213403 A1 | 9/2011 | Aboytes | |
| 2011/0264185 A1* | 10/2011 | Haslinger | A61F 2/958 623/1.11 |
| 2011/0270383 A1* | 11/2011 | Jow | A61F 2/915 623/1.16 |
| 2012/0009325 A1 | 1/2012 | Storment | |
| 2012/0283768 A1 | 11/2012 | Cox et al. | |
| 2012/0296407 A1 | 11/2012 | Caselnova | |
| 2012/0330348 A1 | 12/2012 | Strauss et al. | |
| 2013/0317409 A1 | 11/2013 | Cully et al. | |
| 2014/0012363 A1 | 1/2014 | Franano et al. | |
| 2014/0018838 A1 | 1/2014 | Franano et al. | |
| 2014/0081314 A1 | 3/2014 | Zaver et al. | |
| 2014/0135812 A1 | 5/2014 | Divino et al. | |
| 2014/0163601 A1 | 6/2014 | Stamberg | |
| 2014/0364895 A1 | 12/2014 | Hines | |
| 2015/0005804 A1 | 1/2015 | Franano et al. | |
| 2015/0133994 A1 | 5/2015 | Amplatz et al. | |
| 2016/0030050 A1 | 2/2016 | Franano et al. | |
| 2016/0206321 A1 | 7/2016 | Connor | |
| 2017/0245864 A1 | 8/2017 | Franano et al. | |
| 2017/0258612 A1 | 9/2017 | Franano et al. | |
| 2017/0258613 A1 | 9/2017 | Franano et al. | |
| 2020/0155333 A1 | 5/2020 | Franano et al. | |
| 2020/0163784 A1 | 5/2020 | Franano et al. | |

FOREIGN PATENT DOCUMENTS

| | | |
|---|---|---|
| CN | 101843949 A | 9/2010 |
| CN | 101945624 A | 1/2011 |
| CN | 102770091 A | 11/2012 |
| CN | 103476349 A | 12/2013 |
| DE | 10302241 A1 | 8/2004 |
| EP | 0 101 012 A2 | 2/1984 |
| EP | 1 982 655 A1 | 10/2008 |
| EP | 2055343 A2 | 5/2009 |
| JP | 2007236472 A | 9/2007 |
| JP | 2009521287 A | 6/2009 |
| JP | 2012-512718 A | 6/2012 |
| WO | 97/17911 A1 | 5/1997 |
| WO | 99/03404 A1 | 1/1999 |
| WO | 99/05977 A1 | 2/1999 |
| WO | 99/07294 A1 | 2/1999 |
| WO | 99/60932 A1 | 12/1999 |
| WO | 2000/27292 A1 | 5/2000 |
| WO | 01/52752 A1 | 7/2001 |
| WO | 02/38038 A2 | 5/2002 |
| WO | 02/051320 A2 | 7/2002 |
| WO | 02/080782 A1 | 10/2002 |
| WO | 02/087449 A1 | 11/2002 |
| WO | 03/011363 A2 | 2/2003 |
| WO | 03/061528 A1 | 7/2003 |
| WO | 2004/030518 A2 | 4/2004 |
| WO | 2004/091712 A2 | 10/2004 |
| WO | 2004/112656 A2 | 12/2004 |
| WO | 2006/074410 A2 | 7/2006 |
| WO | 2007/006139 A1 | 1/2007 |
| WO | 2007/092103 A2 | 8/2007 |
| WO | 2008/063455 A1 | 5/2008 |
| WO | 2009/027530 A1 | 3/2009 |
| WO | 2009/045764 A1 | 4/2009 |
| WO | 2009/134337 A1 | 11/2009 |
| WO | 2009/135166 A2 | 11/2009 |
| WO | 2010/028310 A2 | 3/2010 |
| WO | 2012/099704 A2 | 7/2012 |
| WO | 2012/099909 A2 | 7/2012 |
| WO | 2012 099910 A2 | 7/2012 |
| WO | 2013/109309 A1 | 7/2013 |
| WO | 2014/146001 A2 | 9/2014 |
| WO | 2016/044647 A2 | 3/2016 |

OTHER PUBLICATIONS

International Search Report PCT/US2012/000030 (WO 2012/099704 A3) dated Aug. 7, 2012 (4 pages).

International Search Report for PCT/US2012/021620 dated Aug. 3, 2012; (5 pages).

Written Opinion for PCT/US2012/021620 dated Aug. 3, 2012; (13 pages).

International Search Report for PCT/US2012/021621 dated Aug. 16, 2012 (6 pages).

Written Opinion for PCT/US2012/021621 dated Aug. 16, 2012 (20 pages).

Extended European Search Report from related European Application No. 12736401.6, dated Oct. 2, 2014; 11 pgs.

Extended European Search Report from related European Application No. 12737004.7, dated Oct. 2, 2014; 12 pgs.

Extended European Search Report from related European Application No. 12865636.0, dated Aug. 6, 2015; 10 pgs.

International Search Report and Written Opinion from related International Application No. PCT/US2012/047072, dated Dec. 20, 2012; 26 pgs.

International Search Report and Written Opinion from related International Application No. PCT/US2014/030869, dated Nov. 7, 2014; 26 pgs.

Office Action from related Australian Patent Application No. 2012207386, dated Nov. 14, 2015; 3 pgs.

Office Action from related Australian Patent Application No. 2012207387, dated Jan. 21, 2016; 2 pgs.

Office Action from related Australian Patent Application No. 2012207618, dated Jan. 22, 2016; 2 pgs.

First Office Action from related Chinese Patent Application No. 201280005574.7, dated Nov. 21, 2014; 8 pgs.

Second Office Action and Search Report from related Chinese Patent Application No. 201280005574.7, dated Jun. 30, 2015; 21 pgs.

(56) References Cited

OTHER PUBLICATIONS

Third Office Action from related Chinese Patent Application No. 201280005574.7, dated Jan. 19, 2016; 7 pgs.
First Office Action and Search Report from related Chinese Patent Application No. 201280005586.X, dated Dec. 2, 2015; 13 pgs.
First Office Action and Search Report from related Chinese Patent Application No. 201280008971.X, dated Aug. 21, 2015; 16 pgs.
Office Action from related Japanese Application No. 2013-549436, dated Nov. 17, 2015; 13 pgs.
Office Action from related Japanese Application No. 2013-549618, dated Nov. 17, 2015; 12 pgs.
Office Action from related Japanese Application No. 2013-549617, dated Nov. 17, 2015; 7 pgs.
Office Action from related Russian Application No. 2013128987, dated Feb. 17, 2016; 13 pgs.
Office Action from related Russian Patent Application No. 2013138347, dated Dec. 30, 2015; 15 pgs.
Office Action from related Russian Application No. 2013138406, dated Jan. 13, 2016; 15 pgs.
Office Action from related U.S. Appl. No. 13/980,274, dated Feb. 22, 2016; 20 pgs.
Office Action from related U.S. Appl. No. 13/980,274, dated Jun. 2, 2015; 18 pgs.
Office Action from related U.S. Appl. No. 13/980,274, dated Sep. 5, 2014; 10 pgs.
Office Action from related U.S. Appl. No. 13/980,276, dated Feb. 25, 2016; 22 pgs.
Office Action from related U.S. Appl. No. 13/980,276, dated Jun. 1, 2015; 17 pgs.
Office Action from related U.S. Appl. No. 13/980,276, dated Sep. 5, 2014; 10 pgs.
International Search Report and Written Opinion from related International Application No. PCT/US2015/050783, dated Apr. 11, 2016; 15 pgs.
Office Action from related Japanese Application No. 2013-549436, dated Nov. 8, 2016; 10 pgs.
Office Action from related Japanese Application No. 2013-549618, dated Nov. 8, 2016; 9 pgs.
Office Action from related Japanese Application No. 2013-549617, dated Nov. 8, 2016; 8 pgs.
Second Office Action from related Chinese Patent Application No. 201280008971.X, dated Jul. 5, 2016; 3 pgs.
Fourth Office Action from related Chinese Patent Application No. 201280005574.7, dated May 25, 2016; 3 pgs.
Office Action from related Israeli Patent Application No. 227465, dated Oct. 25, 2016; 4 pgs.
Second Office Action from related Chinese Patent Application No. 201280005586.X, dated Oct. 19, 2016; 7 pgs.
Office Action from related Russian Patent Application No. 2013138347, dated Apr. 5, 2016; 25 pgs.
Office Action from related Israeli Patent Application No. 227439, dated Oct. 11, 2016; 4 pgs.
Office Action from related Russian Patent Application No. 2013138406, dated May 12, 2016; 24 pgs.
Office Action from related Israeli Patent Application No. 227440, dated Oct. 6, 2016; 4 pgs.
Office Action from related Russian Patent Application No. 2013128987, dated May 25, 2016; 6 pgs.
Office Action from related Japanese Patent Application No. 2014-552181, dated Jul. 5, 2016; 4 pgs.
Office Action from related Russian Patent Application No. 2014133717, dated Jun. 27, 2016; 5 pgs.
Office Action from related Russian Patent Application No. 2015144196, dated Jun. 15, 2016; 1 pg.
Office Action from related U.S. Appl. No. 14/372,967, dated Nov. 14, 2016; 19 pgs.
Notice of Allowance from related U.S. Appl. No. 13/980,274, dated Dec. 6, 2016; 12 pgs.
Notice of Allowance from related U.S. Appl. No. 13/980,276, dated Dec. 7, 2016; 10 pgs.
Extended European Search Report from related European Application 14762932.3, dated Sep. 16, 2016; 10 pgs.
Office Action from related Australian Patent Application No. 2012366236, dated Oct. 12, 2016; 2 pgs.
Office Action from related Australian Patent Application No. 2012366236, dated Sep. 22, 2017; 3 pgs.
Office Action from related Australian Patent Application No. 2014232323, dated Feb. 6, 2018; 5 pgs.
Office Action from related Australian Patent Application No. 2016256789, dated Aug. 7, 2017; 2 pgs.
Office Action and Search Report from related Canadian Patent Application No. 2,823,378, dated Oct. 30, 2017; 4 pgs.
Office Action and Search Report from related Canadian Patent Application No. 2,822,311, dated Sep. 7,2017; 4 pgs.
Office Action and Search Report from related Canadian Patent Application No. 2,824,284, dated Sep. 6, 2017; 6 pgs.
Office Action from related European Patent Application No. 12736401.6, dated Nov. 21, 2017; 4 pgs.
Office Action from related European Patent Application No. 12865636.0, dated Apr. 3, 2017; 6 pgs.
Office Action from related European Patent Application No. 14762932.3, dated Aug. 30, 2017; 4 pgs.
Decision of Refusal from related Japanese Application No. 2013-549436, dated Jun. 27, 2017; 4 pgs.
Pre-appeal report from related Japanese Application No. 2013-549436, dated Nov. 28, 2017; 6 pgs.
Decision of Refusal from related Japanese Application No. 2013-549618, dated Jun. 27, 2017; 4 pgs.
Pre-appeal report from related Japanese Application No. 2013-549618, dated Nov. 28, 2017; 7 pgs.
Decision of Refusal from related Japanese Application No. 2013-549617, dated Jun. 27, 2017; 5 pgs.
Pre-appeal report from related Japanese Application No. 2013-549617, dated Nov. 28, 2017; 7 pgs.
Final Office Action from related Japanese Application No. 2014-552181, dated Jun. 20, 2017; 5 pgs.
Third Office Action from related Chinese Patent Application No. 201280008971.X, dated Feb. 27, 2017; 8 pgs.
Third Office Action and Search Report from related Chinese Patent Application No. 201280005586.X, dated May 9, 2017; 12 pgs.
First Office Action and Search Report from related Chinese Patent Application No. 201280067371.0, dated Mar. 1, 2016; 23 pgs.
Second Office Action from related Chinese Patent Application No. 201280067371.0, dated Jan. 12, 2017; 14 pgs.
Third Office Action from related Chinese Patent Application No. 201280067371.0, dated Sep. 13, 2017; 14 pgs.
First Office Action and Search Report from related Chinese Patent Application No. 201480027636.3, dated Oct. 17, 2016; 19 pgs.
Notice of Amendment from related Chinese Patent Application No. 201580062443.6, dated Jul. 20, 2017; 3 pgs.
Notice of Amendment from related Chinese Patent Application No. 201710994867.7, dated Dec. 11, 2017; 3 pgs.
Office Action from related U.S. Appl. No. 14/372,967, dated Aug. 9, 2017; 24 pgs.
Office Action from related U.S. Appl. No. 14/777,412, dated Jan. 25, 2018; 20 pgs.
Office Action from related Israeli Patent Application No. 227439, dated Nov. 28, 2017; 4 pgs.
Office Action from related Israeli Patent Application No. 227440, dated Jan. 8, 2018; 4 pgs.
Office Action from related New Zealand Patent Application No. 711474, dated Jun. 27, 2017; 7 pgs.
Office Action from related Russian Patent Application No. 2013138347, dated Jun. 2, 2017; 55 pgs
Office Action from related Russian Patent Application No. 2013138406, dated Sep. 5, 2017; 21 pgs.
Office Action from related Russian Patent Application No. 2013128987, dated Jul. 25, 2017; 7 pgs.
Decision on Grant from related Russian Patent Application No. 2013128987, dated Dec. 1, 2017; 18 pgs.
Office Action from related Russian Patent Application No. 2014133717, dated Aug. 17, 2017; 8 pgs.

(56) References Cited

OTHER PUBLICATIONS

Decision on Grant from related Russian Patent Application No. 2014133717, dated Dec. 5, 2017; 14 pgs.
Office Action from related Russian Patent Application No. 2017112929, dated May 26, 2017; 4 pgs.
Office Action and Search Report from related Taiwan Patent Application No. 103110016, dated Jun. 30, 2017; 12 pgs.

* cited by examiner

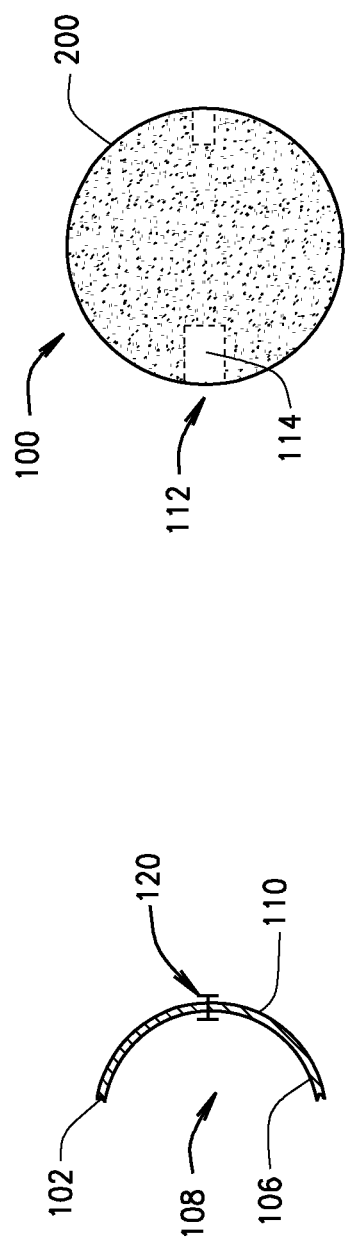
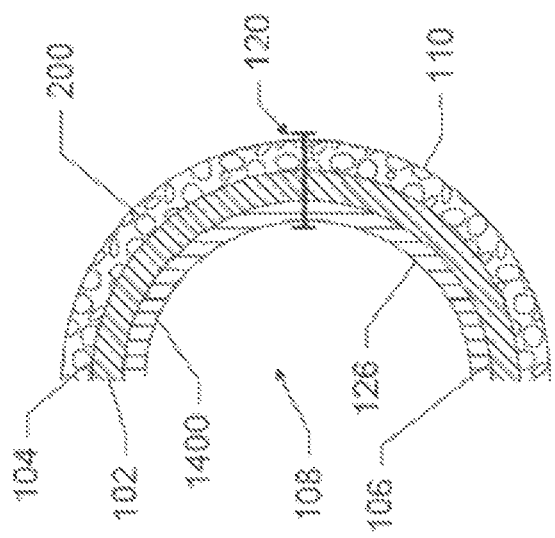
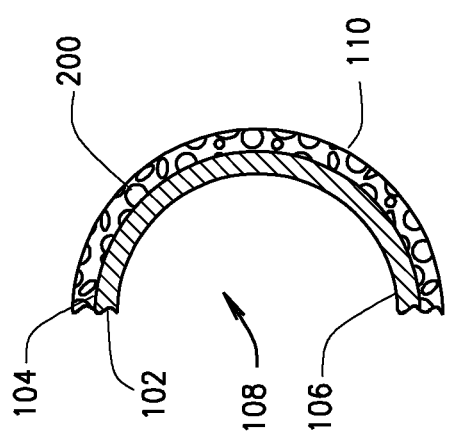
FIG. 2A
FIG. 2B
FIG. 2C
FIG. 1E

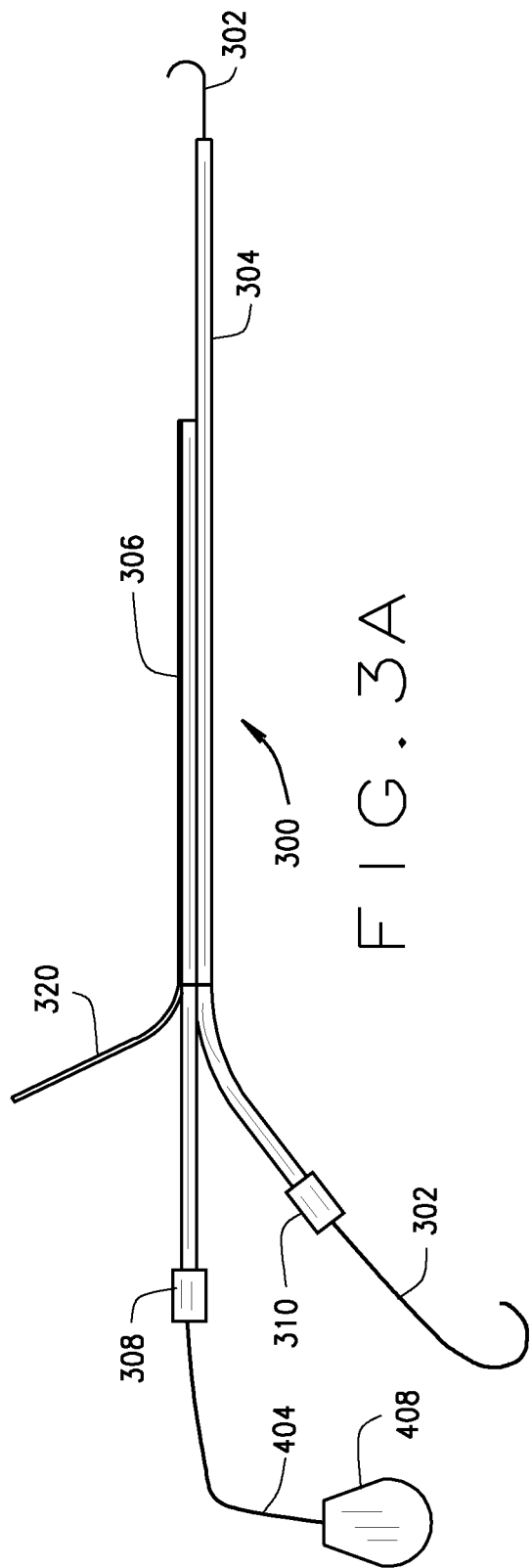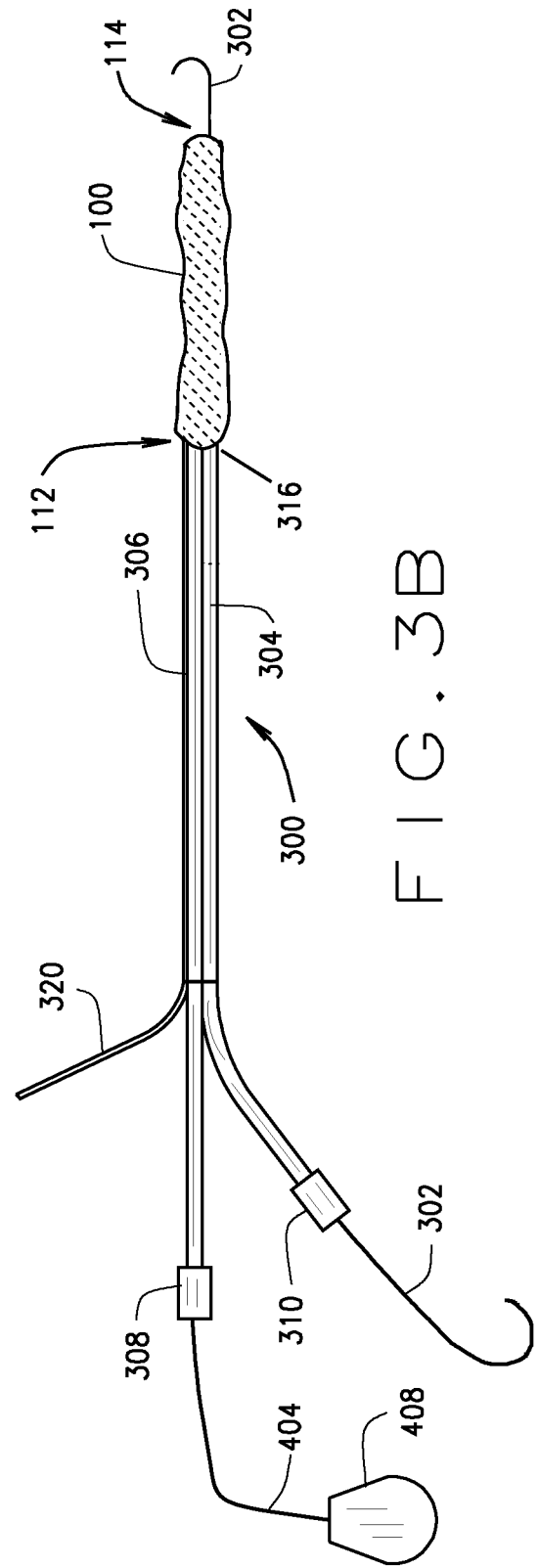

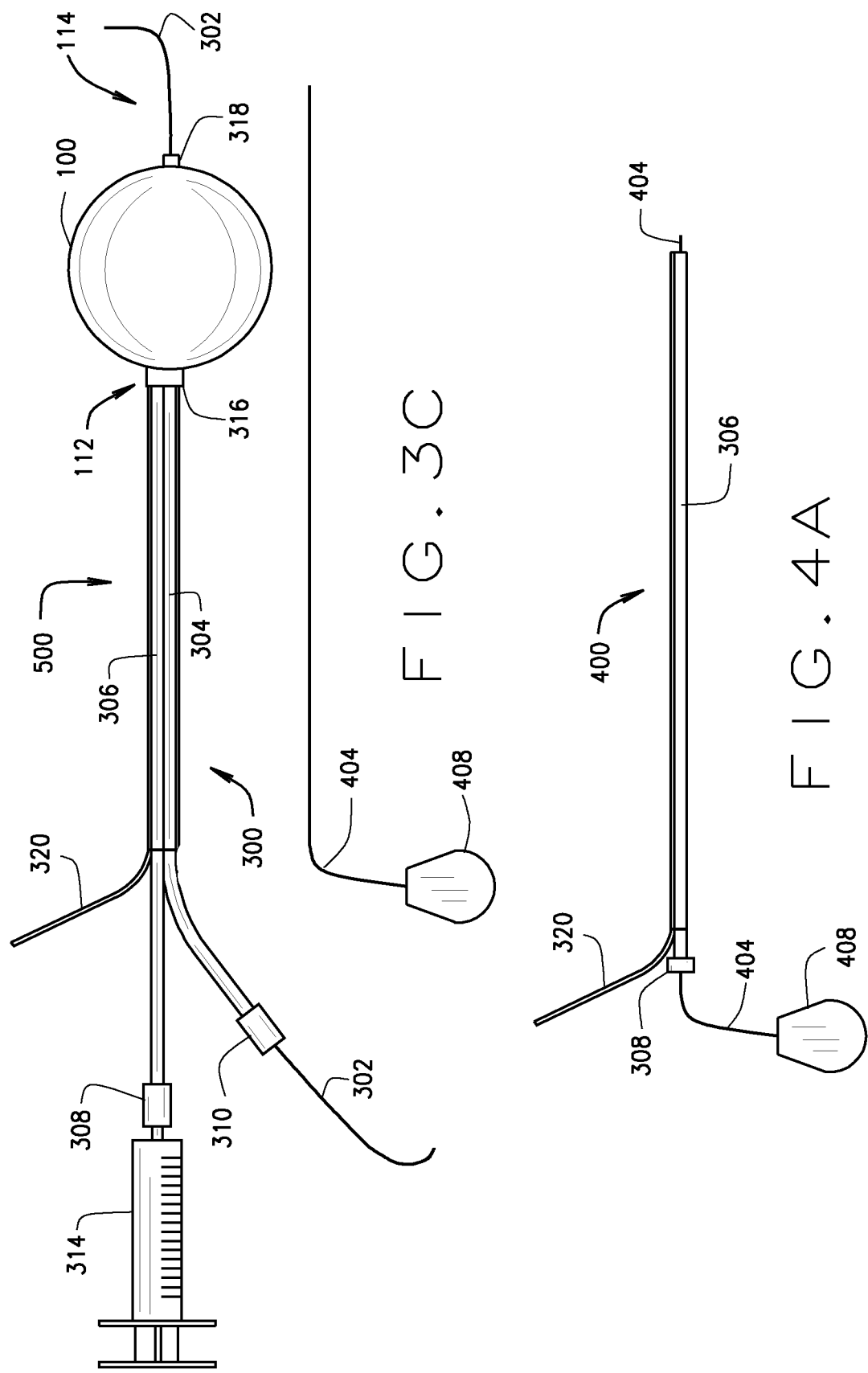

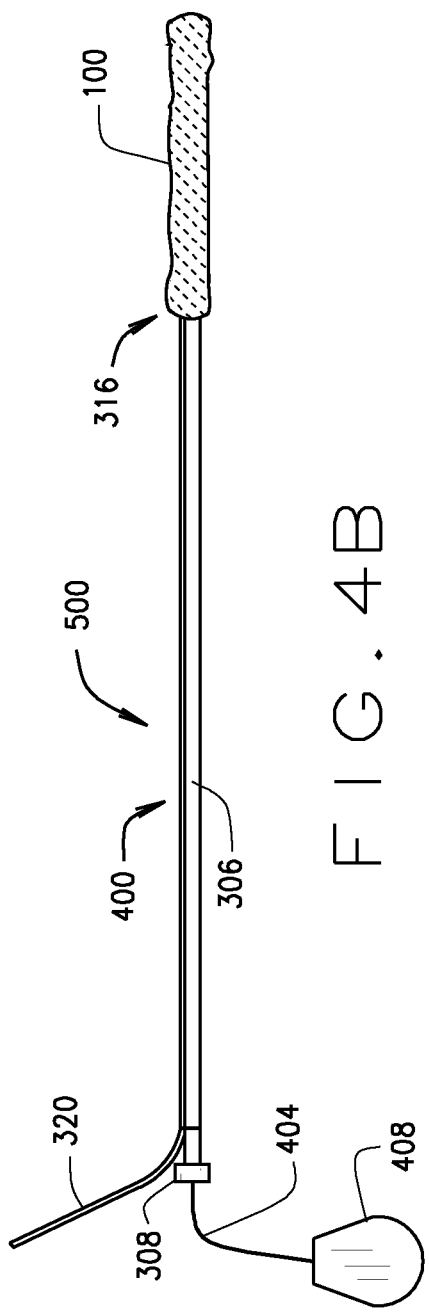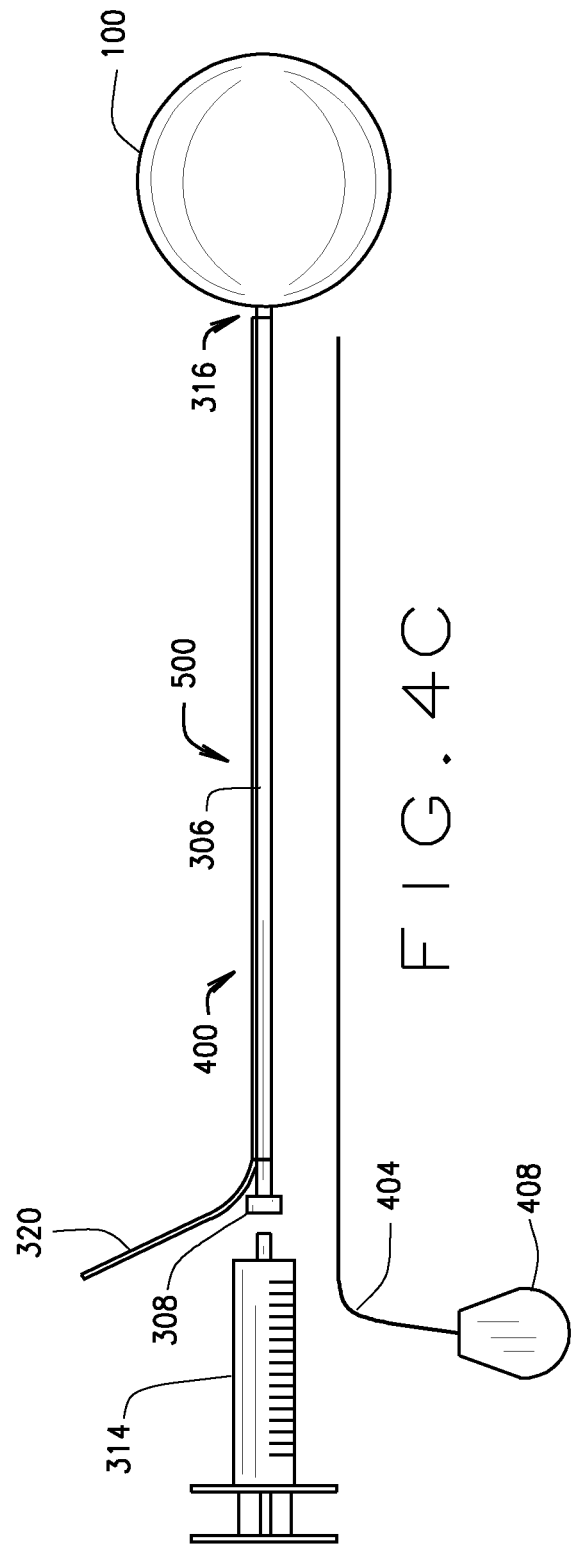

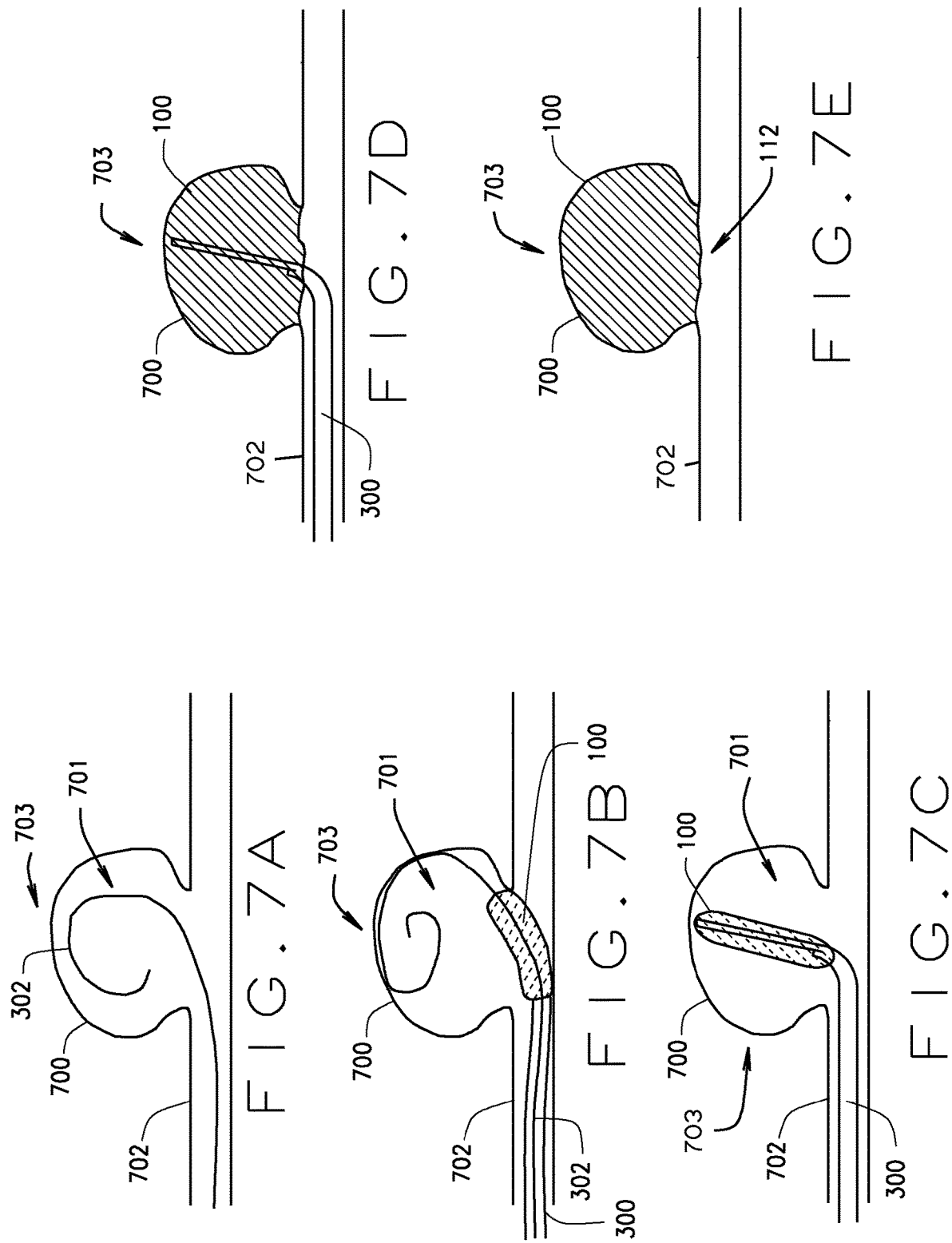

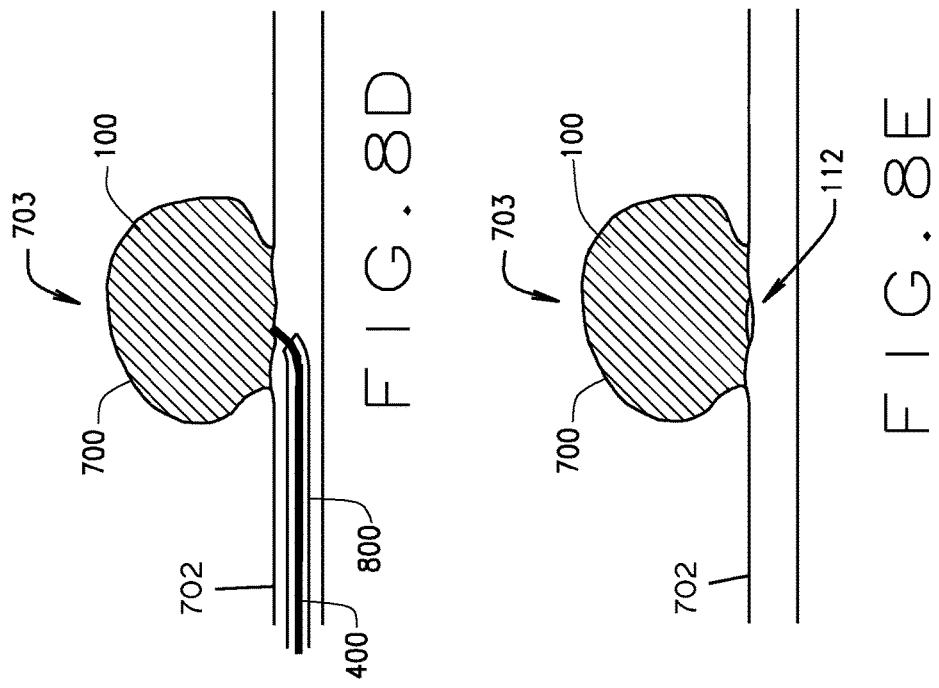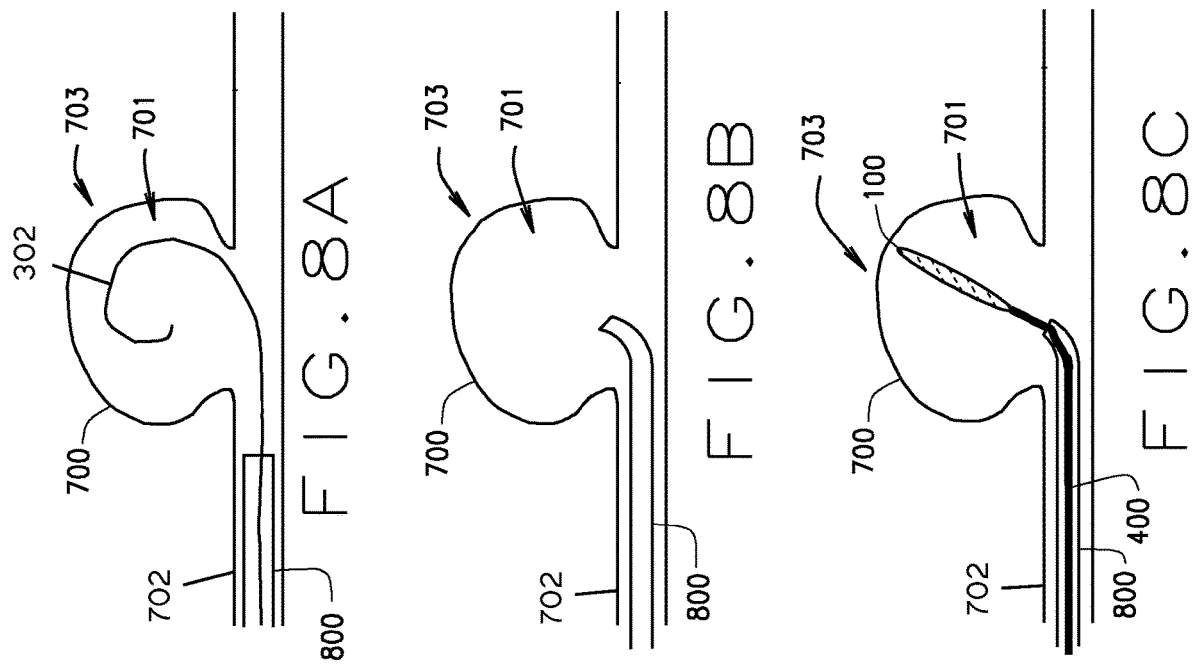

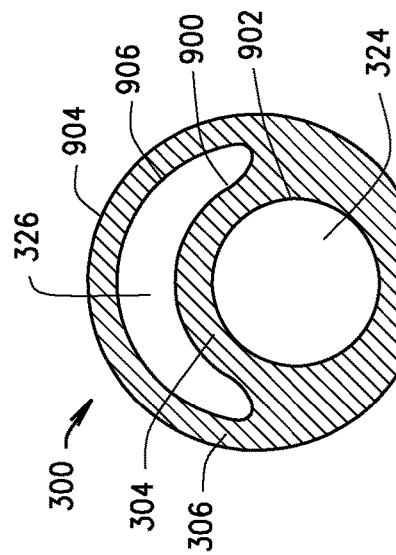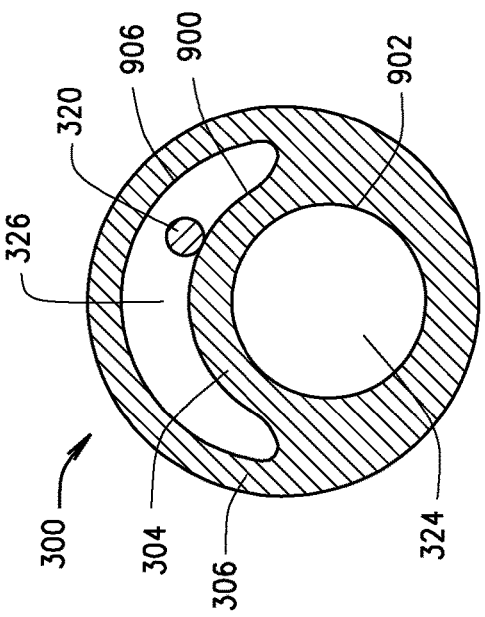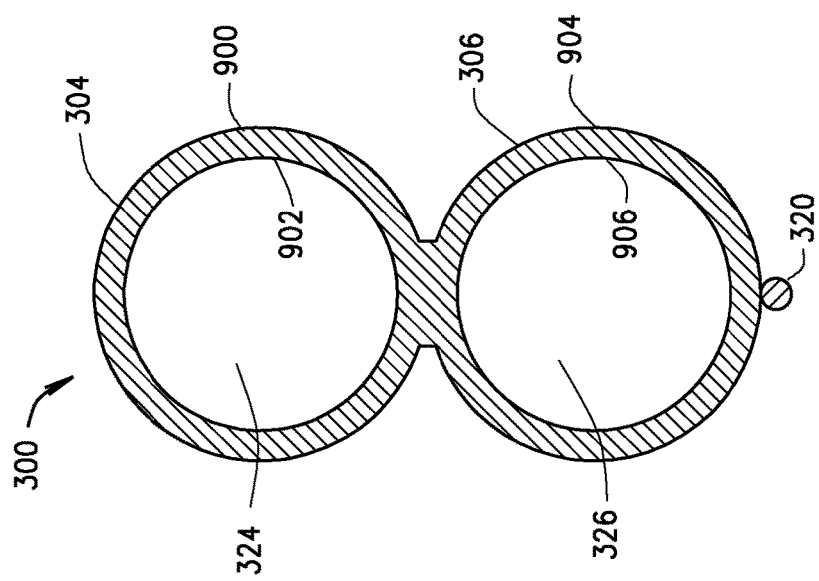

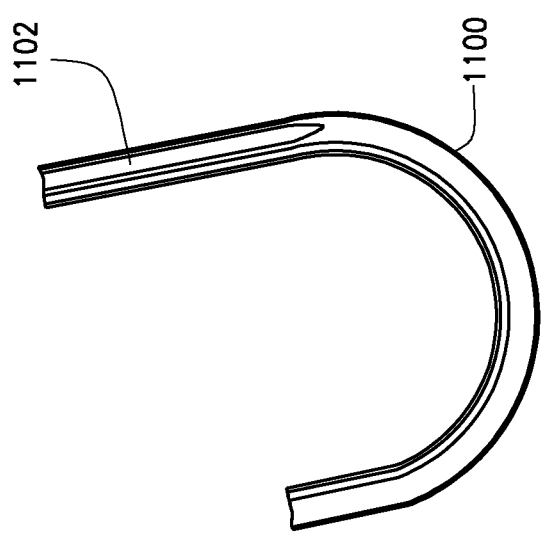
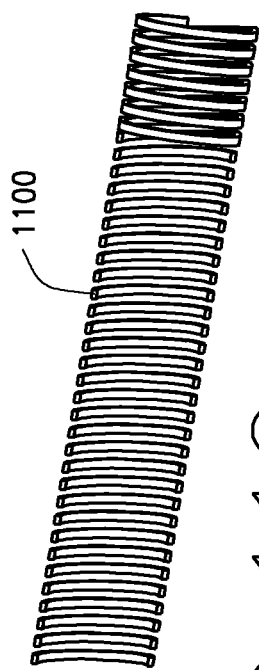
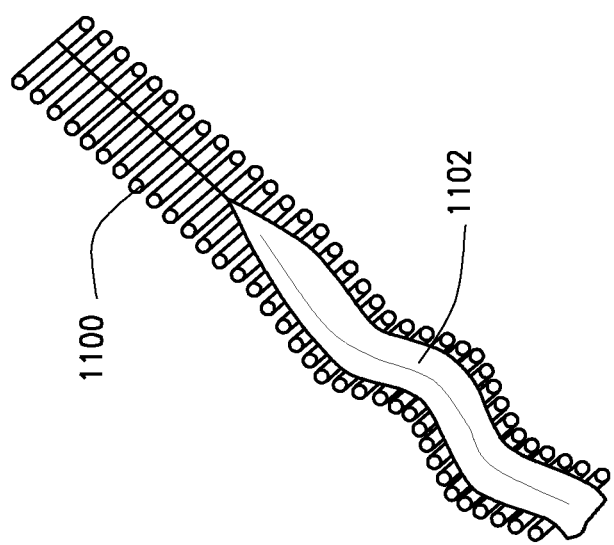

DETACHABLE METAL BALLOON DELIVERY DEVICE AND METHOD

CROSS REFERENCE TO RELATED APPLICATIONS

This application is a U.S. National Patent Application of PCT/US2012/21620 filed Jan. 17, 2012, which claims the benefit of U.S. Provisional Patent Application No. 61/433,305 filed Jan. 17, 2011, the disclosure of which is incorporated herein by reference in their entirety for all purposes.

FIELD OF THE INVENTION

The invention relates to various forms of an expandable, detachable metal balloon that can be delivered to a desired location within the body utilizing a delivery device. The invention further relates to methods of attaching the balloon to a catheter delivery device, compressing the balloon, positioning the compressed balloon into the lumen of a selected segment of a blood vessel or an aneurysm, inflating and expanding the balloon, and then separating the balloon from the catheter such that the balloon remains in place in an expanded state while the catheter is removed. Further, the invention relates to various delivery devices, including catheters, for positioning and inflating or expanding the balloon in a desired location.

BACKGROUND OF THE INVENTION

Sven-Ivar Seldinger, the Swedish pioneer in angiography adapted flexible wires for insertion into blood vessels as a means to support catheters during their advancement in blood vessels. Catheters containing balloons have subsequently been developed and used to occlude blood vessels. In certain instances, the balloon portion of these catheters can be separated or "detached" from the catheter portion and left in the body while the catheter portion is removed, often for the purpose of permanently occluding blood vessels. Traditional detachable balloons are formed from compliant, nonporous materials such as silicone that can be inflated and expanded by stretching with a fluid or a gas, and contain a valve to maintain balloon pressure after detachment of the balloon from the catheter.

Over time, it was discovered that compliant detachable silicone balloons had major drawbacks. First, the smooth surface and the material properties of the balloons did not promote the incorporation of tissue from the wall of occluded blood vessels. Therefore, the detached balloons were prone to migration, and moving to non-target locations within the vascular system, thus resulting in the occlusion of non-target blood vessels. Second, the valves on these balloons would often leak and the compliant balloons would then deflate, increasing the risk of balloon movement and resulting in unacceptable rates of vessel recannulization. Finally, when inflated, these balloons are resilient, and resistant to reshaping after inflation and detachment. Finally, the surfaces of these balloons are not particularly suitable for delivering medicines or other pharmacologically active molecules.

More recently, short segments of coiled metal wire (coils) have gained favor as medical devices for occluding blood vessels and vascular aneurysms. In order to treat a blood vessel or aneurysm with coils, an operator inserts a catheter into a lumen of the vascular system and maneuvers the catheter tip to the desired location. With the catheter tip in position, the operator passes small coils through the catheter into the lumen of the vessel or the cavity of the aneurysm. Many coils are often required to fully occlude a vessel or aneurysm, resulting in high costs and long treatment times. Also, coils may inadvertently move away from the treatment location during the procedure and occlude non-target vessels, thereby compelling the operator to retrieve the coils from the non-target location.

Other prior devices utilizing metal balloons for treating aneurysms require inflation and then a deflation to be effective. For example, U.S. Patent Publication No. 2007/0288083 by Hines describes a bi-lobed metal balloon wherein one lobe of the balloon is inserted into an aneurysm while the other remains in the parent vessel, and then both lobes are inflated and then deflated such that each lobe forms a flattened disc that covers one side of the opening between the blood vessel and the aneurysm. This medical device has some drawbacks. For example, a void remains in the lumen of the aneurysm that could result in incomplete aneurysm thrombosis or recannulization. In addition, a portion of the collapsed device protrudes into the lumen of the adjacent parent vessel, resulting in some degree of vessel narrowing and irregularity, which increases the risk of thrombus formation, intimal hyperplasia and stenosis of the treated vessel.

Therefore, there is a need for a medical device with a detachable metal balloon that can be inflated to fill a void, detached from the delivery device while remaining inflated, without the need for a valve, and can be subsequently shaped to fit the desired void. Moreover, it is desired to have a device that provides local drug delivery.

SUMMARY OF THE INVENTION

The invention relates to a balloon that can be delivered to a desired location utilizing a variety of devices and is made of a material that can expand to a rigid or semi-rigid expanded form. The invention further relates to methods of placing the compressed balloon into the lumen of a blood vessel or aneurysm, inflating and expanding the balloon, and then detaching the balloon from the delivery device while leaving the balloon in place in an expanded or inflated state. Further, the invention relates to a variety of delivery devices such as catheters for positioning, and inflating and expanding the balloon at a desired location. A catheter and a modified infusion wire are examples of such delivery devices. As such, the invention can be used to treat an aneurysm, for example, by leaving an expanded metal balloon in the aneurysm. Further, the surface of the metal balloon can be configured to promote tissue in-growth and release drugs, pharmacologically active molecules, or pharmacologic compositions.

The present invention relates to a balloon comprising a rigid or semi-rigid material such as a metal for use in treating a blood vessel or an aneurysm or other vascular abnormality. In one embodiment, the balloon is a single-lobed metal balloon having a wall with an interior surface, an exterior surface, and a wall thickness ranging between about 3 μm and 60 μm. The balloon also has an opening that allows for the passage of fluid. The wall of the balloon defines an opening having a diameter ranging between about 0.1 mm and about 20 mm. In one embodiment, the balloon has an exterior layer located on the exterior surface of the wall. The exterior layer has a porous construction and is made of a spongy metal, for example, or any other porous material that can hold fluid or solid material, including drugs, pharmacologically active molecules, or pharmacologic compositions. Any composition can be used that promotes thrombosis or tissue proliferation. The balloon may have an expanded diameter ranging from about 2 mm to about 100 mm, an expanded volume ranging from about 0.004 cc to about 100 cc, and an expanded length between about 2 mm to about 120 mm.

The balloon optionally has a neck, or stem, that defines the opening that can remain open or be sealed upon detachment. The wall of the balloon may be made of metal selected from the group consisting of gold, platinum, silver, titanium, vanadium, aluminum, nickel, tantalum, zirconium, chromium, silicon, magnesium, niobium, scandium, cobalt, palladium, manganese, molybdenum, alloys thereof, and combinations thereof. Other rigid materials, or combination of materials, can be used so long as they can be expanded from a compressed state to an expanded state and remain expanded in the body, holding their shape under usual conditions. The exterior layer may be made of a metal selected from the group consisting of gold, platinum, silver alloys thereof, and combinations thereof.

In another embodiment, the exterior layer has a plurality of pores ranging in diameter from about 0.05 μm to about 100 μm. The exterior layer also includes a suspension of drugs, pharmacologically-active molecules, or pharmacological compositions including those that promote thrombosis, such as thrombin, Ethiodol®, Sotradecol®, platelet derived growth factor, and combinations thereof or those that promote cell and tissue growth.

In another embodiment, two or more medical device balloons may be used in combination to fill a void. Additionally, a second, third, or more balloons may be required to fill the remaining void not filled by the first balloon. The balloons of these devices typically have an exterior layer on the exterior surface of the balloon wall. The exterior layer of these metal balloons can be made porous, allowing the growth of tissue into the wall of the balloon or configured to release drugs, pharmacologically active molecules, or pharmacologic compositions.

The present invention also relates to a method of treating an aneurysm, occluding a blood vessel, or treating other vascular abnormalities with a detachable metal balloon. The method includes the steps of positioning the balloon at a desired location using a delivery device, inflating and expanding the balloon with a fluid, and detaching the delivery device from the balloon while leaving the balloon in an expanded state at the desired location. In an embodiment, the balloon is made of a ductile material.

In another embodiment, the method also includes the steps of: accessing the blood vessel with a needle, inserting a guide wire through the needle, removing the needle, and optionally, inserting a vascular sheath into the blood vessel. The method also includes the steps of positioning the guide wire at the desired location, inserting the catheter delivery device, advancing the catheter delivery device over the guide wire, and positioning it at the desired location. The method also includes the steps of inflating and expanding the balloon, detaching the balloon from the catheter delivery device, removing the catheter delivery device, removing the wire, and removing the sheath. The balloon is inflated so that at least 50% to at least 90% of the balloon exterior surface contacts the surface of the void. The balloon exterior surface optionally includes a porous exterior layer having pores range in diameter from about 0.05 μm to about 100 μm.

In another embodiment, the method also includes the steps of: accessing the blood vessel with a needle, inserting a guide wire through the needle, removing the needle, and optionally, inserting a vascular sheath into the blood vessel. The method also includes the steps of advancing the catheter to the desired position by advancing it over the guide wire, removing the guide wire, inserting the wire delivery device through the lumen of the catheter, and positioning it at the desired location. The method also includes the steps of inflating and expanding the balloon, detaching the balloon from the wire delivery device, removing the wire delivery device, removing the catheter, and removing the sheath. The balloon is inflated so that at least 50% to at least 90% of the balloon exterior surface contacts the surface of the void. The balloon exterior surface optionally includes a porous exterior layer having pores range in diameter from about 0.05 μm to about 100 μm.

In other embodiments, the method further includes the steps of placing a solution or suspension of a pharmaceutical, drug, or pharmacologically active molecules into an exterior layer of a balloon exterior surface and delivering the pharmaceutical, drug, or pharmacologically active molecules to the desired location by positioning the expanded balloon at the desired location and leaving it in place where at least some of the molecules leave the balloon and diffuse into the surrounding tissues. The method may also include welding or soldering an opening of the balloon to the delivery device and detaching the balloon from the delivery device by electrolysis to dissolve the weld or solder between the balloon and the delivery device. The method may also include gluing the balloon to the delivery device and detaching the inflated, expanded balloon from the delivery device by mechanical means, or by electrolysis of a metal portion of the balloon itself. Additional steps may include applying an external force to the opening of the expanded, detached balloon to seal the balloon after detachment from the delivery device.

The present invention also relates to a delivery device for positioning and inflating a metal balloon. The device includes a detachable single-lobed metal balloon similar to the balloon described above. The device also includes a catheter that has, or can be connected to, a fluid source, a guidance member for advancing the catheter to a desired location, and a detachment member for detaching the catheter from the balloon. Alternative to a catheter, a modified infusion wire can be used whereby the infusion wire is comprised of a coil member wrapped around a wire core. In practice, once positioned, the wire core is removed and the newly created lumen is used to deliver fluid from the wire hub to the balloon to cause expansion by inflation.

As such, the guidance member can be any device or system to position the medical device at the desired location. Typically, the guidance member is a flexible guide wire. The flexible guide wire may have a soft rounded-tip or a j-shaped tip.

The detachment member can be any device or system to detach the balloon from the catheter. An exemplary detachment member is an elongated electrolysis wire. The electrolysis wire may be an insulated conductive wire that carries an electrical current to dissolve a weld or solder between the catheter and the balloon, thereby detaching or separating the catheter from the balloon. Alternatively, the electrolysis wire may be an insulated conductive wire that carries an electrical current to dissolve a metal portion of the balloon itself, thereby detaching or separating the catheter from the balloon. In another embodiment, the opening of the balloon is welded to the delivery device and the balloon is detached from the delivery device by electrolysis that dissolves the weld. Alternatively, a mechanical detachment may occur where the catheter is physically separated from the balloon.

The catheter includes one or more hollow cylindrical members that define one or more lumens. Typically, the catheter is a single-lumen catheter or a double-lumen catheter, where a first cylindrical member is dimensioned to deliver fluid from the fluid source to the balloon, once the balloon is in place, and a second cylindrical member is dimensioned to pass over the guidance member. If a single cylindrical member is used, the fluid is delivered from the fluid source to the balloon through the single cylindrical member and the device is advanced into position through the lumen of a separate catheter which acts to guide the device.

The balloon may be attached to the outside of the catheter. In one embodiment, the balloon is folded to form one or more pleats prior to or after attaching the balloon to the outside of the catheter, and the pleats are rolled and compressed, similar to the folding of non-compliant angioplasty balloons. In various other embodiments, the pleated balloon is folded and compressed to fit on the end of a flexible guide wire and travel within a hollow cylindrical member of a separate catheter. The folded, compressed balloon travels through a lumen of the catheter, where it emerges at the desired location. Once at the desired location and outside of the catheter used for guidance, the balloon can be inflated and expanded, and separated from the delivery device.

In a particular embodiment, the catheter has a hollow cylindrical member that defines a lumen. The cylindrical member has a proximal end that is attached, or can be attached to a fluid source. The cylindrical member is made of a polymer blend and has a wall thickness ranging from about 0.05 mm to about 0.5 mm. The defined lumen has a diameter ranging from about between 0.15 mm to about 2.2 mm. The catheter may also include a second cylindrical member to accept a guide wire. In various other embodiments, the detachment member is located on the outer surface of a cylindrical member and the fluid source delivers a gas, liquid, or a combination thereof to the balloon through a cylindrical member. In other embodiments, the balloon is attached to the catheter prior to insertion. The attachment may be made via metal weld, gluing, or crimping.

As such, a balloon and delivery device is provided that can be utilized to deliver a balloon to occlude a biological conduit such as an artery or vein, or an abnormality of a biological conduit such an aneurysm.

In another embodiment, the fluid that is used to inflate and expand the balloon can contain drugs or pharmacologically active molecules that catalyze the formation of thrombus.

DESCRIPTION OF FIGURES

FIGS. 1A-E depict embodiments of the metal balloon of the detachable metal balloon medical device.

FIGS. 2A-C depict embodiments of the metal balloon of the detachable metal balloon medical device FIG. 3A depicts a longitudinal view of an embodiment of the catheter portion of the detachable metal balloon medical device.

FIGS. 3B-C depict longitudinal views of an embodiment of the detachable metal balloon medical device.

FIG. 4A depicts a longitudinal view of an embodiment of the catheter portion of the detachable metal balloon medical device.

FIGS. 4B-C depict longitudinal views of an embodiment of the detachable metal balloon medical device.

FIGS. 7A-E depict a sequence of positioning, expanding, and detaching the balloon with an embodiment of the detachable metal balloon medical device.

FIGS. 8A-E depict a sequence of positioning, expanding, and detaching the balloon with an embodiment of the detachable metal balloon medical device.

FIGS. 9A-E depict axial cross-sectional views of embodiments of the detachable balloon delivery device.

FIGS. 11A-C depict embodiments of removable core wires that may be used as the catheter portion of the detachable metal balloon medical device.

DETAILED DESCRIPTION OF THE INVENTION

Figure 1A:
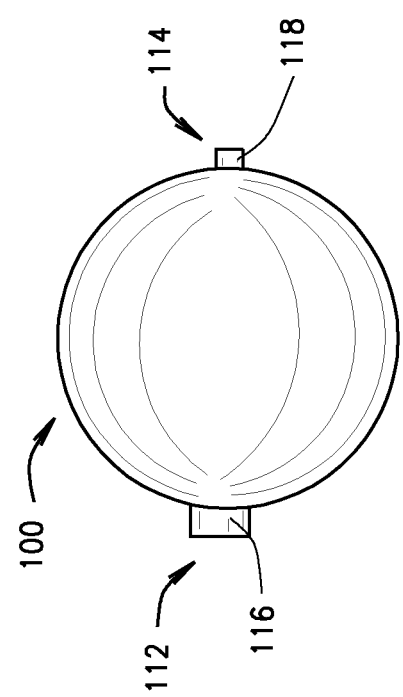
Figure 1B:
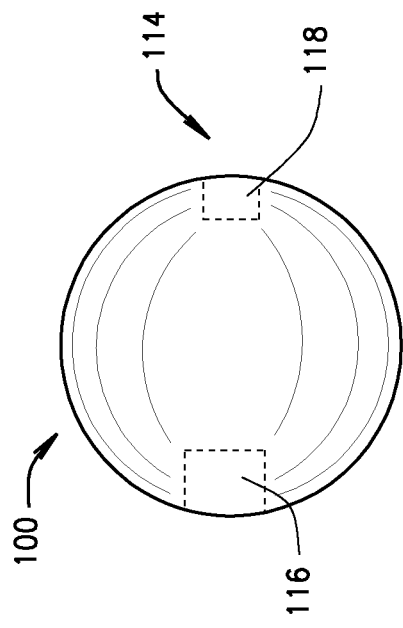
Figure 1C:
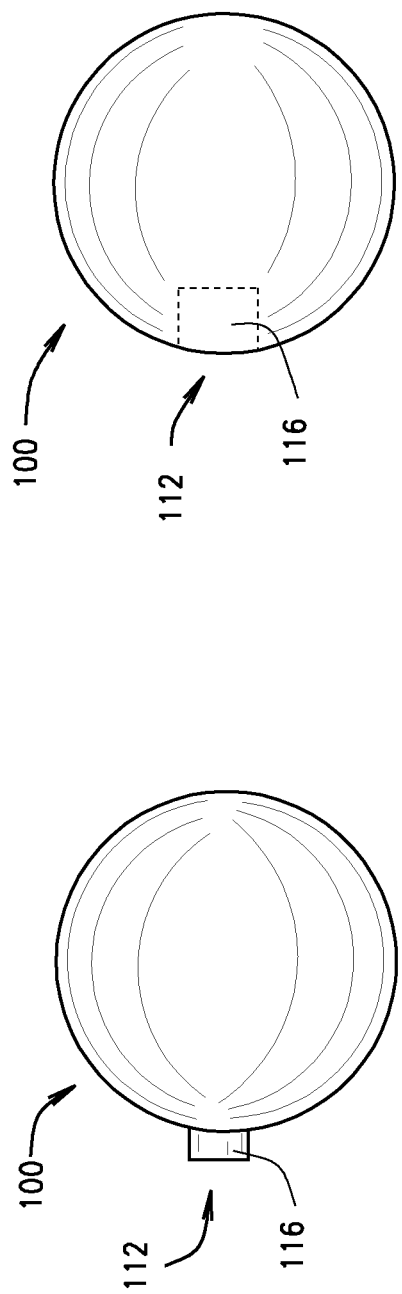
Figure 1D:
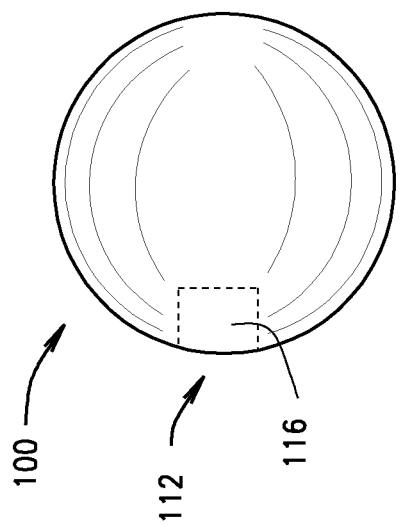

The detachable metal balloon 100 of the present invention, as shown in FIGS. 1A-E, is a balloon that once positioned, is inflated and expanded and remains in an expanded state to occlude blood vessels and treat a number of vascular conditions or abnormalities, including aneurysms. A delivery device, such as a catheter 300, is used to deliver the balloon 100 to a desired location. The medical device 500, including a catheter and the attached balloon, as shown in FIGS. 3-6, can be used as part of a method to occlude a blood vessel or treat a vascular condition or abnormality, such as an aneurysm.

The detachable metal balloon 100 may be composed of a single continuous layer or wall 102, as shown in FIG. 1E. Alternatively, the balloon 100 may contain a single continuous wall 102 and additional layers including one or more porous layers 104, as shown in FIGS. 2A-C. The balloon 100 has an interior surface 106 that when inflated and expanded with a fluid defines a space or void 108. The balloon 100 has an exterior surface 110 that, when expanded, contacts the internal wall of the blood vessel or vascular structure. A fluid is a substance having particles that easily move and change their relative position without a separation of the mass. Fluids that can be used to inflate or expand the balloon 100 include liquids, gases, and combinations thereof.

The exterior layer 104 can have a number of pores 200 that may contain drugs, pharmacologically active molecules, or pharmaceutical compositions. Advantageously, the balloon 100 can be delivered to the desired location, inflated and expanded, and then detached from the delivery device, such as the catheter 300, in an expanded state. The expanded balloon 100 will typically conform to the shape of the cavity in which it is placed, but can also be shaped with external force, such as a physical force applied by an adjacent expanded angioplasty balloon. Additionally, multiple detached metal balloons 100 can be utilized to fill the desired void. Finally, the invention specifically relates to a detachable metal balloon that remains in the lumen or void of a blood vessel or aneurysm in an expanded state.

The metal balloon 100 is attached to a delivery device, such as a catheter 300, and delivered to the desired location. Any delivery device member that can deliver the balloon 100 through the vascular lumen, inflate or expand the balloon, and separate therefrom is generally acceptable.

Inflating or expanding the balloon, as used herein, refers to the partial or complete distention of the balloon 100 using a fluid, a solid, or a combination thereof. In various embodiments, the balloon 100 need not be fully distended to occlude a blood vessel. For example, the balloon 100 may be partially or completely inflated using a fluid. In another example, the balloon 100 may be partially or completely expanded using a solid material alone or in combination with fluid inflation. In all embodiments, the balloon remains in an expanded state after detachment from the delivery device. An expanded state refers to the at least partial distention of the balloon 100, such as at least 10%, 20%, or 50% of the maximum balloon volume.

A catheter is a tubular medical device for insertion into canals, vessels, passageways, or body cavities to permit the injection or the withdrawal of fluids. Catheters designed for insertion into the lumen of blood vessels are typically flexible and are often comprised of plastic or metal. In certain situations, a catheter is placed into the body with a wire or trochar that occupies the lumen defined by the tubular portion of the catheter. Once placed, the wire or trochar can be removed in order to allow the injection or withdrawal of fluids.

A wire is metal in the form of a usually very flexible thread or slender rod. The basic angiography guide wire consists of a fixed solid metal core covered by a metal spring coil. An infusion wire is a modified guide wire wherein the solid metal core can be removed, leaving a lumen that can be used to inject or withdraw fluids, such as a solution of tissue plasminogen activator, a protein that catalyzes the breakdown of blood clots. In this way, an infusion wire having a removable core wire can be used as a catheter. FIGS. 11A-C depict various examples of an infusion wire with a metal spring coil wire 1100 and a removable core wire 1102. FIG. 11C depicts a partial cross-section of the modified guide wire 1100 with the core wire 1102 removed.

Preferably, the delivery device is a catheter 300, as shown in FIGS. 3A-C, which can carry the balloon 100 to the desired site. The catheter 300 must also allow for passage of fluid used to inflate and expand the balloon. A catheter 300 is defined as at least one hollow cylindrical member that defines a lumen, with the catheter designed and dimensioned such that it can be inserted in the body to deliver the balloon 100 to a desired location, inflate or expand the balloon, and separate therefrom. The catheter 300 will include at least one hollow cylindrical member, and more likely two hollow cylindrical members. When the catheter includes two cylindrical members, one cylindrical member can operate with a guidance member, such as a guide wire 302, to guide the device to the desired location. A detachment member can also be utilized with the catheter, whereby the detachment member is carried on the outer surface or in the wall of one of the cylindrical members or is passed through the lumen of one of the cylindrical members. The second cylindrical member delivers fluid to inflate or expand the balloon 100, which can be located on the outer wall of the cylindrical member(s). An alternative includes a single cylindrical member through which fluid passes through the cylindrical member to inflate and expand the balloon and the medical device is advanced through a separate catheter for the purpose of guiding it to the desired location where it can be inflated, expanded, and detached.

The method of the present invention includes delivering the balloon 100 to a desired location and then inflating and expanding it to an expanded state. Once expanded, the delivery device (typically the catheter 300) is separated from the balloon 100, which remains expanded. Detachment can be accomplished via mechanical separation, such as by using another cylindrical member surrounding the catheter to shear the balloon from the tip of the delivery catheter, or by way of electrolysis. The expanded balloon 100 fills at least a portion of the lumen of the blood vessel or the aneurysm, thereby reducing the risk of subsequent bleeding from the blood vessel or aneurysm. Optionally, the exterior layer 104 of the expanded balloon 100 releases drugs or pharmacologically active molecules to increase the formation of thrombus on the exterior surface 110 of the balloon 100 and within the cavity of the aneurysm. Optionally, the porous exterior layer 104 allows the growth of adjacent tissue into the metal surface. As part of the method, the delivery device can be positioned using a guide wire 302, which has been placed near the treatment area. In this embodiment, the delivery device is advanced over the guide wire into position, and the guide wire 302 is then removed. Alternatively, as part of the method, the balloon 100 can be positioned using a guide catheter 800, wherein a delivery device attached to the balloon, as shown in FIGS. 8A-E, is passed through the lumen of the guide catheter and into the cavity of the aneurysm 701, inflated or expanded, and then separated from the delivery device.

Balloon

As discussed and illustrated in FIGS. 1A-E, the balloon 100 has one or more openings 112 and 114 defined by the wall 102 or by one or more necks 116 and 118. Fluid can enter the opening 112 to expand the space or void 108 defined by the interior surface 106. The interior surface 106 and the exterior surface 110 define a balloon wall thickness 120. The balloon 100 is configured to be expanded, and remain expanded after separation from the delivery device.

In various embodiments, one or both of the necks 116 and 118 can project away from the wall 102 or they project into the interior space or void 108. The necks 116 and 118 can be used for attaching the balloon to the delivery device and may play a role in separating the balloon 100 from the delivery device.

The detachable balloon 100 is formed from a metal that can also assume a variety of forms after expansion. Acceptable shapes include circular, cylindrical, or oblong, as well as shapes defined by the aneurysm lumen void. An embodiment where the balloon 100 has a generally tubular form can be used to treat fusiform aneurysmal dilations of blood vessels. This embodiment can also be used to occlude normal diameter blood vessels for various purposes, including treating bleeding from the blood vessels or their branches.

In various embodiments, the dimensions of the balloon 100 are selected upon the condition being treated. In one preferred embodiment, the inflated diameter of the balloon 100 ranges from about 2 mm to about 100 mm. Similarly, a preferred inflated volume for the balloon ranges from about 0.005 cc to about 65 cc. In one embodiment, the balloon 100, preferably, has an inflated length between about 2 mm to about 120 mm. Preferably, the balloon wall thickness 120 ranges between about 3 µm and 60 µm, while the opening 112 has a diameter ranging between about 0.1 mm and about 20 mm.

The balloon 100 is made from one or more biocompatible and ductile metals. By way of example and not limitation, the metal can be selected from the group consisting of gold, platinum, silver, titanium, vanadium, aluminum, nickel, tantalum, zirconium, chromium, silicon, magnesium, niobium, scandium, cobalt, palladium, manganese, molybdenum, alloys thereof, and combinations thereof. In a preferred embodiment, the wall 102 of the balloon 100 is continuous while the external layer 104 of the balloon 100 is made of a porous metal that is comprised of gold. In another embodiment, one or both of the wall 102 and the external layer 104 are formed of one or more biocompatible and ductile metals. In one embodiment, the wall 102 and/or the exterior layer 104 are formed by electroforming or electroplating. In other embodiments, the wall 102 and/or the exterior layer 104 may be composed of rubber, plastic, polymer, woven or knitted fiber materials, other semi-rigid materials, or combinations thereof, configured such that the balloon 100 is to remain in an expanded state after expansion and detachment, even where the pressure inside and outside the balloon are the same or similar. For one specific embodiment, the exterior layer is comprised of Parylene™.

In various embodiments, the wall 102 is solid, while the exterior layer 104 is porous, as shown in FIGS. 2A and 2B. The porous or spongy nature of the exterior layer 104 can be configured to contain drugs, pharmacologically active molecules, or pharmaceutical compositions within the pores 200. As such, drugs, pharmacologically active molecules, or pharmaceutical compositions can be delivered to the treatment site. The drugs, pharmacologically active molecules, or pharmaceutical compositions are incorporated into the pores 200 of the exterior layer 104 prior to positioning the balloon 100 at the desired location. The drugs, pharmacologically active molecules, or pharmaceutical compositions may be delivered into the pores 200 via capillary or wicking action. The pores 200 range from about 0.05 μm to about 100 μm in diameter. The pore diameters for each balloon may be selected to deliver specific drugs, pharmacologically active molecules, or pharmaceutical compositions at a specific rate. By way of example and not limitation, the balloon 100 may have a porous exterior layer 104 where the pore diameter averages from about 0.05 μm to about 5 μm, about 5 μm to about 25 μm, or about 25 μm to about 100 μm.

The drugs, pharmacologically active molecules, or pharmaceutical compositions may be incorporated directly into the pores of the exterior layer 104 or they may be incorporated as solutions and/or suspensions. By way of example and not limitation, the pharmaceuticals may include thrombin, Ethiodol®, and Sotradecol®, or combinations thereof. Other drugs, pharmacologically active molecules, or pharmaceutical compositions that promote thrombosis and coagulation or stimulate the growth of adjacent tissue into the porous external wall of the balloon 100 may also be used. Such drugs or pharmacologically active molecules may include molecules to promote cell or tissue growth, such that the balloon 100 will become physically attached to the tissue at the treatment location. The dosages and manner in which the drugs or pharmacologically active molecules are incorporated into the exterior layer 104 are a matter of choice depending on the treatment performed.

Figure 12:
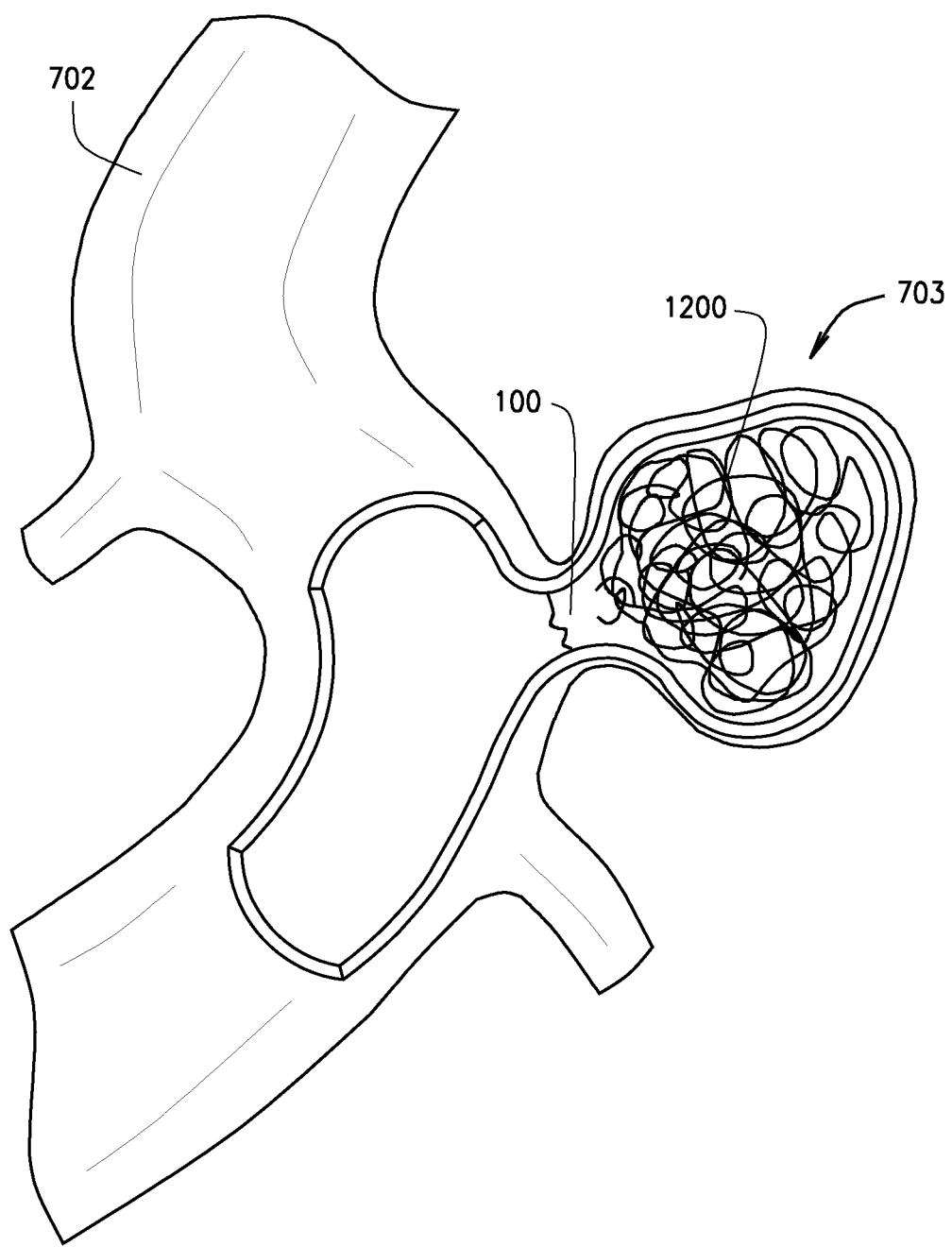
FIG. 12 depicts an embodiment of the detachable metal balloon filled with one or more coils or support structures.

In various embodiments, the wall 102 and the external layer 104 are composed of different biocompatible metals. In other embodiments, the wall 102 and the external layer 104 are composed of the same metal. Over time, the balloon 100 remains expanded with the balloon eventually becoming affixed to the surrounding tissue. In another embodiment, as shown in FIG. 12, the balloon 100 can be filled with solid members 1200 such as metallic or polymeric coils, metallic or polymeric expansile structures, beads, balls, microspheres, or combinations thereof. Other suitable biocompatible solid materials may also be used.

Alternatively, the balloon 100 may comprise an additional liner or layer on the interior surface of the wall 1400, as shown in FIG. 2C. The additional liner or layer on the interior surface of the wall of the balloon 100 may be composed of polymer, plastic, latex, or rubber, woven or knitted fiber materials, metals, other materials, or combinations thereof. Preferably, the interior layer 1400 is an elastomeric coating that is bonded to the interior surface 106 of the wall 102. The interior layer 1400 can be a variety of thicknesses, preferably ranging between about 0.5 μm and about 59 μm. The total thickness of the exterior layer, interior layer, and wall will be between about 3 μm and about 60 μm, regardless if a wall or the wall and two layers are used. In a preferred embodiment, the interior layer 1400 is Parylene™, however, latex, or other elastomers may be used. The interior layer 1400 adds mechanical properties (such as strength) to the wall 102. Further, the interior layer 1400, optionally, can form a seal that prevents the escape of fluids from the balloon 100, should the metal portion of the wall contain a defect. The balloon wall 102 and any additional layers define an interior surface 106 or 126 such that when the balloon is expanded, with a fluid, liquid, gas, or solid, an internal space or void 108 is defined.

In another embodiment, the exterior and/or the interior of the balloon neck 116 or balloon may be coated with an insulating substrate such as a polymer such as Parylene™, while a portion of the balloon or balloon neck remains uncoated. The uncoated portion may be intentionally left uncoated during the coating process or may be exposed after coating by laser ablation or other suitable processes. After expansion, the uncoated portion of the balloon or balloon neck may be electrically coupled with an electrolysis wire 320 or other insulated conductive wire for conducting electricity, and an electrical current can be passed from power source to the uncoated portion of the balloon or balloon neck to perform electrolysis, and dissolve, at least a portion of the uncoated portion, thereby separating the expanded balloon 100 from the delivery catheter.

Delivery Device

The delivery device may be a single lumen as shown in FIGS. 4A-C or a multi-lumen catheter as shown in FIGS. 3A-C. For example, one potential catheter 300 comprises two hollow cylindrical members or tubes that define lumens to form a dual lumen catheter. One lumen is for the passage of a guidance member, such as a guide wire 302, and the second lumen is for the passage of fluids or gases into the balloon for inflating and expanding the balloon 100. With a generally rounded form to the metal balloon, this embodiment can be used to treat focal, eccentric, rounded, and saccular aneurysmal dilations, or aneurysms, of blood vessels. The catheter 300 can be configured to pass through vascular system, such as with the balloon 100 in a compressed form. The catheter 300 includes a detachment member, such as the electrolysis wire 320 shown in FIG. 3C, for separating the catheter from the balloon thereby allowing the expanded balloon 100 to remain in place while the catheter is removed from the body.

In one embodiment, the hollow cylindrical member has a wall thickness ranging from about 0.05 mm to about 0.5 mm. Preferably, the cylindrical wall thickness ranges from about 0.05 mm to about 0.15 mm. The lumen defined by the cylindrical member has a diameter ranging from about 0.15 mm to about 2.2 mm. In a preferred embodiment, the lumen diameter ranges from about 0.7 mm to about 1.57 mm. In one embodiment, the catheter 300 is configured with the balloon 100 attached to the external surface of the catheter in a deflated, compressed, and/or pleated form. The catheter 300 is advanced over the guide wire 302 until the compressed balloon 100 is at the desired position, where the balloon is expanded and separated from the catheter. In another embodiment, the balloon 100 is attached to the catheter 300 in a deflated, compressed, and/or pleated form. The catheter 300 is configured to pass completely through the lumen of a larger guidance catheter until the compressed balloon 100 is at the desired position, where the balloon is expanded and separated from the catheter.

The catheter 300 is composed of a biocompatible material. By way of example, and not limitation, the catheter 300 and various components thereof may be composed of silicone rubber, natural rubber, polyvinyl chlorides, polyurethane, copolyester polymers, thermoplastic rubbers, silicone-polycarbonate copolymers, polyethylene ethyl-vinyl-acetate copolymers, woven polyester fibers, or combinations thereof. In one embodiment, the wall of the hollow cylindrical member may be reinforced with a metal, such as braided stainless steel or nitinol, to enhance control and reduce kinking of the catheter 300 during use.

Figure 5:
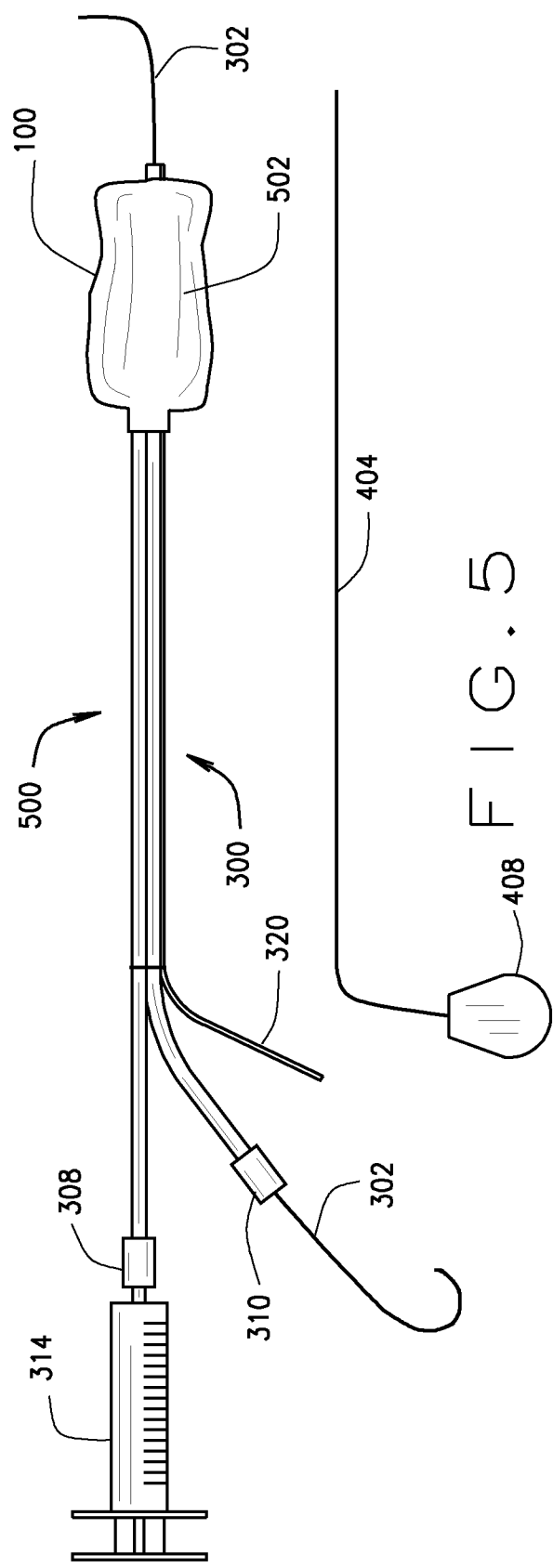
FIG. 5 depicts a longitudinal view of an embodiment of the detachable metal balloon medical device, wherein the balloon is inflated.

By way of example and not limitation, the guidance member may be a separate flexible guide wire 302, as depicted in FIGS. 3, 5, and 7. The guide wire 302 is preferably a straight, soft-tipped angiographic wire of sufficient length to reach the desired location with a distal end of the guide wire, while a proximal end extends out and away from the point of entry into the vascular system. In one embodiment, the guide wire 302 has a curved J-shaped distal tip, typically constructed from a memory alloy or a braided metal that causes the tip to return to the J-shape after any applied stress is removed.

FIG. 3A depicts longitudinal views of an embodiment of the catheter portion of the detachable metal balloon medical device. FIGS. 3B-C depict longitudinal views of an embodiment of the detachable metal balloon medical device 500. The catheter 300 moves over the guide wire 302 to deliver the balloon 100, deliver a fluid to inflate and expand the balloon, and then separate therefrom. The catheter 400 can include a single hollow cylindrical member or tube that defines a lumen (as in FIGS. 4, 6, and 8) or the catheter 300 can include multiple hollow cylindrical members defining a number of lumens (as in FIGS. 3, 5, and 7). As shown, a suitable construction for an embodiment of the catheter 300 includes a first hollow cylindrical member 304 and a hollow cylindrical member 306 that are adjacent and parallel to one another. The hollow cylindrical members 304 and 306 define two lumens. One lumen 326, a fluid or gas delivery lumen, provides fluid or gas to inflate and expand the balloon. The other lumen 324, a guidance member lumen, accepts the guide wire 302 that is used to help position the balloon 100 at the desired location. In one embodiment, the hollow cylindrical members 304 and 306 may be housed within a third hollow cylindrical member (not shown). In other embodiments, the first hollow cylindrical member 304 may be located within the second hollow cylindrical member 306 or the hollow cylindrical members may be coaxial.

The proximal end of the first hollow cylindrical member 306 includes a balloon inflation or expansion port 308. The balloon inflation or expansion port 308 allows the hollow cylindrical member 306 to communicate with a pressurized fluid or gas source, such as a syringe 314 or a pump (not shown) containing, for example, a water, saline or radiopaque solution.

Potential fluids provided by the pressurized fluid source include liquids, gases, or combinations thereof. By way of example and not limitation, the fluid may be water, a saline solution, a radiographic contrast solution, or a mixture or any of the three. In one embodiment, the fluid may further include a solution or suspension of drug or pharmacologically active molecules to induce tissue growth and/or thrombosis at the site of the balloon inflation. In another embodiment, the fluid suspends a number of solids, such as wires, coils, support structures, or acrylic gelatin microspheres that aid in inflating or expanding and maintaining the expanded shape of a balloon 100.

The proximal end of the hollow cylindrical member 304 includes a guide wire port 310. The guide wire port 310 facilitates the insertion of the guide wire 302 into the hollow cylindrical member 304. The guide wire 302 is fed through the hollow cylindrical member 304 and extended out of the distal end of the catheter 300. In this embodiment, the catheter 300 is advanced over the guide wire 302 and positioned in the selected segment of a blood vessel or into the lumen of a vascular aneurysm. Once the catheter 300 is in the desired position, the removable wire 404 is withdrawn from the delivery device, the balloon 100 is inflated or expanded by fluid provided to the hollow cylindrical member 306 by the syringe 314 connected to the balloon inflation port 308. With the guide wire 302 removed, the guide wire port 310 and the hollow cylindrical member 304 can be used to infuse fluids such as saline, radiographic contrast agents, or solutions of drugs such as thrombin, or can be used to aspirate fluids or blood.

The dimensions of the catheter 300 are a matter of design choice depending upon the size of the particular blood vessels or cavities in which it is to be used. For example, the medical device 500 may be used to occlude very small blood vessels or biological conduits, as in the brain, where the diameter of the device prior to inflation or expansion may be approximately 2-5 Fr. In another example, the medical device 500 may be used to occlude larger blood vessels such as venous varices. In this example, the diameter of the catheter may be approximately 2-10 Fr. In various embodiments, the catheter 300 may be dimensioned to occlude non-vascular biological conduits or abnormal communications between biological spaces such as enterocutaneous fistulas. The length of the catheter 300 is also a matter of design choice depending on the distance between the entry point into the body and the location to be treated. By way of example and not limitation, catheter lengths can range between about 5 cm and about 300 cm.

In one embodiment, the balloon 100 has one or more openings, such as the opening 112, that are attached to the distal end of the hollow cylindrical member 306. Alternatively, the balloon 100 may have two openings, where the first opening 112 is attached to the distal end of the hollow cylindrical members 306 and 304 and the second opening 114 is attached to the distal end of the hollow cylindrical member 304. In this embodiment, the hollow cylindrical member 304 extends through the interior of the balloon 100. The balloon 100 may be folded, compressed, and/or wrapped around the exterior of the distal end of the catheter 300, as shown in FIG. 3B.

This embodiment of the catheter 300 also includes a detachment member, such as the electrolysis wire 320 or insulated conductive wire that extends along the length of the delivery device. The detachment member is used to separate the balloon 100 from the catheter 300. In one embodiment, the electrolysis wire 320 lies along the exterior surface of the hollow cylindrical member 304, as shown in FIGS. 3C, 5, and 9B.

In various embodiments, the electrolysis wire 320 or insulated conductive wire is an elongated wire that can conduct an electrical current and can be located within a lumen of a cylindrical member, within the wall of a cylindrical member, or attached to the outside of a cylindrical member.

The electrolysis wire 320 is in electrical communication with the weld or solder bond 316 between the balloon 100 and the delivery device. In this embodiment, a direct electrical current or charge (DC current) is applied to the electrolysis wire 320 after the balloon 100 is inflated. The DC current dissolves at least a portion of the weld or solder bond 316, resulting in separation of the expanded balloon and the delivery device and leaving the balloon 100 expanded at the desired position while the delivery device is removed. In another embodiment, the electrolysis wire 320 is in electrical communication with the balloon itself 100, which is attached to the delivery device by an adhesive or other attachment method. In this embodiment, a direct electrical current or charge (DC current) is applied to the balloon 100 after the balloon 100 is inflated. The DC current dissolves at least a portion of the balloon 100, resulting in separation of the remainder of the expanded balloon, and the delivery device, and leaving the balloon 100 expanded at the desired position while the delivery device is removed.

In one embodiment, an opening of the inflated balloon 100 is left open after detachment from the catheter 300. In other embodiments, an opening of the inflated balloon 100 is closed before, during, or after detachment from the catheter 300. By way of example and not limitation, the openings may be sealed by applying an external force, such as with an adjacent angioplasty or shaping balloon. In all embodiments, the balloon 100 retains its expanded shape after detachment and is resistant to compression. The balloon 100 remains expanded even if the pressures inside and outside of the expanded balloon are equal or similar due to rigidity of the wall of the balloon. In another example, maintenance of the balloon expansion is assisted by instilling rigid or semi-rigid material into the balloon 100.

In yet other embodiments, the balloon 100 is not welded to the catheter 300, but temporarily affixed to the catheter, such as by crimping. In these embodiments, the balloon 100 is detached from catheter 300 by friction and/or various tools inserted through or around the catheter.

In other embodiments, the balloon 100 is not welded to the catheter 300, but affixed to the catheter with an adhesive. In these embodiments, the balloon 100 is detached from catheter 300 by friction, electrolysis and/or various tools inserted through or around the catheter.

FIG. 4A depicts longitudinal views of an embodiment of the catheter portion of the detachable metal balloon medical device. FIGS. 4B-C depict longitudinal views of an embodiment of the detachable metal balloon medical device 500. This embodiment includes a single lumen catheter 400 having a single hollow cylindrical member 306 for receiving a removable wire 404. The wall of the catheter can be comprised of a plastic or polymer material, as previously described. In another embodiment, the wall of the catheter is comprised of a wound metal coil. In this embodiment, the hollow cylindrical member 306 and the removable wire 404, in combination, are similar to existing infusion wires. The hollow cylindrical member 306 includes a connection port 308 at a proximal end and is attached to the balloon 100 at a distal end, such as with a weld, an adhesive, or crimping. As shown in FIG. 4B, the balloon 100 may be wrapped, compressed, and or folded along the exterior of hollow cylindrical member 306.

In one embodiment, a catheter 400 with the compressed balloon 100 is advanced through the lumen of a larger guide catheter, as shown in FIGS. 8A-E, to the desired location. The compressed balloon 100 is advanced beyond the distal end of the larger guide catheter and into the desired position. Once the catheter 400 has been placed in the desired location, the wire 404 is removed from the hollow cylindrical member 306, and a fluid source, such as the syringe 314 is connected to the connection port 308 to inflate or expand the balloon 100. The removable wire 404 may include a handle 408 or other device to facilitate wire insertion and removal. After the balloon 100 is expanded, as shown in FIG. 4C, the catheter 400 and the balloon 100 can be separated so that the catheter 400 can be removed while leaving the expanded balloon 100 in the desired position. In one embodiment, after the balloon 100 is inflated or expanded, a DC current is applied to the electrolysis wire 320 to dissolve a weld or solder between the balloon and the catheter 400. Once the weld is dissolved, the catheter 400 is removed while the expanded balloon 100 remains in place. In another embodiment, a DC current is applied to the electrolysis wire 320 to dissolve a portion of the balloon. Once the balloon portion is dissolved, the catheter 400 is removed while the remainder of the expanded balloon 100 remains in place.

Figure 6:
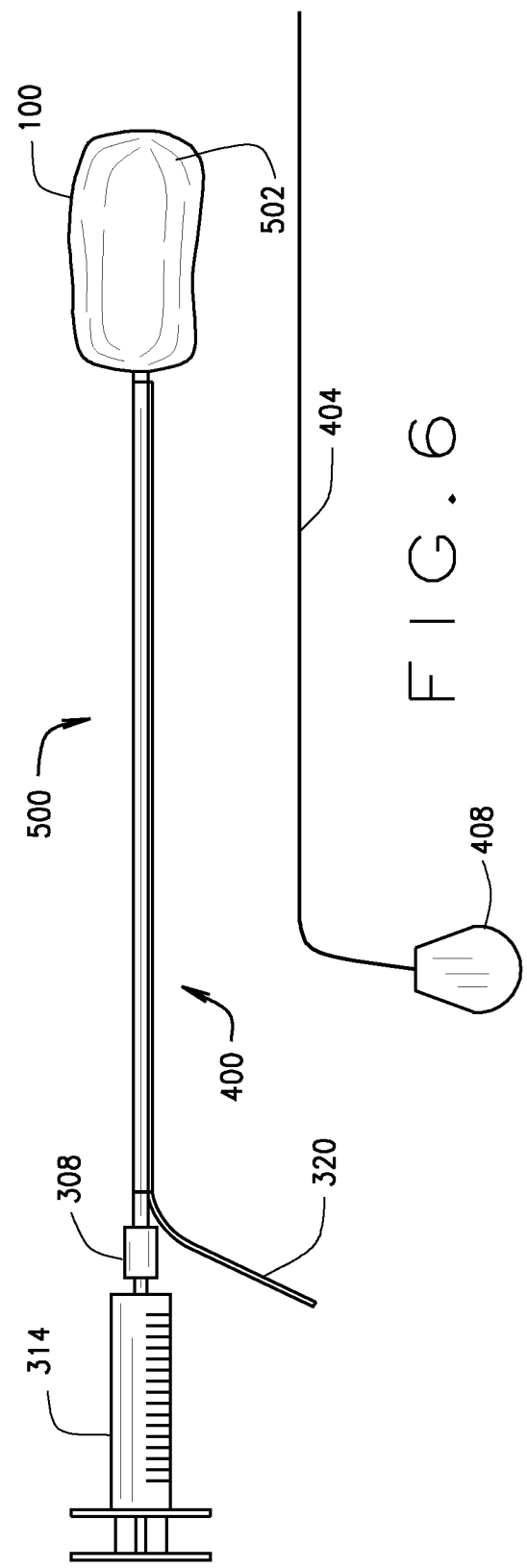
FIG. 6 depicts a longitudinal view of an embodiment of the detachable metal balloon medical device, wherein the balloon is inflated.

FIGS. 5 and 6 depict additional embodiments of the detachable balloon delivery device attached to deflated configurations of the balloon 100. In one embodiment, the balloon 100 is folded into pleats, then the pleats of the folded balloon are wrapped around the catheter 300, and the balloon is compressed against the catheter 300. In another embodiment, the balloon 100 is folded into pleats, then the pleats of the folded balloon are wrapped around the removable wire 404, and then the balloon is compressed against the removable wire 404.

In various embodiments, the balloon 100 is attached to the catheter 300, 400, then the pleats 502 are formed, and then the pleats are wrapped and compressed onto the catheter or the removable wire 404. In another embodiment, the balloon 100 is folded to form the pleats 502, then attached to the catheter 300, 400, and then folded or compressed onto the outer surface of the catheter 300, 400, or the removable wire 404.

Method

The method of the present invention includes a number of steps for delivering the balloon 100 to the desired location, inflating and expanding the balloon 100, and separating the balloon and the delivery device. In one embodiment, the method includes the steps of accessing an artery with a needle and then advancing a guide wire, such as the guide wire 302, through the needle. Next, the needle is removed and optionally a vascular sheath is inserted. Then, the guide wire 302 is further advanced to the desired location. Optionally, a standard angiography catheter is used with the guide wire 302 to advance the guide wire to the desired location. After the guide wire 302 is appropriately placed, the standard angiography catheter is removed from the body. Then, a catheter 300 with a compressed balloon 300 at the distal end is advanced over the guide wire 302 until the catheter is positioned at the desired location. Optionally, the guide wire 302 is then withdrawn, and the balloon 100 is inflated and expanded with a pressurized fluid. The expanded balloon 100 is separated from the catheter 300 and the catheter is removed, along with the guide wire 302. As described above, the method may also include the steps of providing an electrical current to the electrolysis wire 320 to dissolve the weld or solder 316 attaching the balloon 100 to the catheter, or to dissolve a portion of the balloon itself. In one embodiment, the method further includes the step of shaping the expanded balloon 100. Shaping the balloon 100 may be accomplished by the application of external and/or internal forces, such as with an adjacent angioplasty balloon or occlusion-type balloon.

FIGS. 7A-E and 8A-E depict sequences of positioning, expanding, and detaching the balloon 100 within the cavity of an aneurysm of a blood vessel. In FIGS. 7A-E, an aneurysm 703 within the blood vessel 702 is filled with the balloon 100. The balloon 100 is inflated with a pressurized liquid, gas, or combination thereof. In one embodiment, the fluid contains a suspension of coils, beads, and/or a solution or suspension of a drug, pharmacologically active molecules, or pharmaceutical composition.

The expanded shape of the balloon 100 is based upon the abnormality being treated. In one example, the balloon 100 is shaped by both by the shape of the aneurysm lumen or void and also, optionally, by the application of an external force. The external force may be applied by inflating a separate and adjacent balloon (not shown) in the lumen of the blood vessel 702, thereby pushing the wall of the balloon 100 toward the aneurysm. In other embodiments, the balloon 100 is manufactured into a non-spherical orientation to match the contours of the cavity for a particular aneurysm 703. Other shapes and orientations may be used. The exterior surface 110 of the balloon 100 makes contact with a substantial portion of the inner surface 700 of the aneurysm 703. In one embodiment, the exterior surface 110 of the balloon 100 makes contact with at least 50% of the inner surface 700 of the aneurysm 703. In other embodiments, the exterior surface 110 makes contact with over 90% of the inner surface 700. The expanded balloon fills a substantial portion of the lumen of the aneurysm 701. In one embodiment, the expanded balloon fills at least 50% of the lumen of the aneurysm 701.

In FIG. 7E, the catheter 300 and guide wire 302 have been withdrawn and the opening 112 of the balloon 100 remains open. In other embodiments, the opening 112 of the balloon may be closed. In all embodiments, the balloon 100 will remain expanded.

In another embodiment, shown in FIGS. 8A-E, a guidance catheter 800 is used to access the lumen 701 of the aneurysm 703. A single lumen catheter, such as the catheter 400, is then advanced through the guide catheter 800. The catheter 400 is in communication with the opening 112 of the balloon 100. A pressurized fluid is transferred through the catheter 400 into the interior space or void 108 of the balloon so that, when expanded, the balloon 100 shape closely matches the contours of the aneurysm 800. In one embodiment, the balloon 100 is manufactured to a particular shape prior to attachment to the catheter 400.

In all embodiments, the expanded shape of the balloon 100 is determined by four factors: 1) the manufactured shape of the balloon 100; 2) the degree of inflation or expansion; 3) the size and shape of the aneurysm 703; and 4) the effect of any applied external force after inflation or expansion. By way of example and not limitation, the manufactured size and shape of the balloon 100 may be determined by making measurements of the aneurysm 703. The measurements can be made by using medical images and standard distance reference markers. Other methods of measuring the aneurysm may also be used.

In another embodiment, the balloon 100 may be manipulated and configured in vivo or even in situ within the aneurysm 703. In this embodiment, it is not necessary to determine the precise contours of the aneurysm 703 prior to inserting the balloon 100. The balloon 100 is shaped by the application of internal and/or external forces. For example, an external force may be applied by the use of an external angioplasty balloon, or by tools inserted through or around the catheter 400. In other embodiments, the balloon 100 may be shaped in a step prior to or after the step of detaching the balloon from the catheter 400.

In other embodiments, two or more balloons similar to the balloon 100, may be positioned and inflated to fill a portion or all of the lumen of a particular segment of blood vessel, an aneurysm lumen or void, or other body cavities. In these embodiments, pre-shaped balloons, unshaped balloons, malleable balloons, or a combination thereof may be used. In all embodiments, the balloons are positioned to maintain their expanded shapes and resist unintentional compression or deformation.

FIG. 9A depicts an axial cross-sectional view of the dual lumen catheter 300. The hollow cylindrical member 304 has an outer wall 900 and an inner wall 902 and the hollow cylindrical member 306 has an outer wall 904 and an inner wall 906. The cylindrical members 304 and 306 are parallel and adjacent to one another, while the electrolysis wire 320 runs along the outer wall 904 of the hollow cylindrical member 306. FIG. 9B is an alternative to the device in FIG. 9A, with FIG. 9B depicting axial cross-sectional view of an alternative double lumen catheter 300. In one embodiment, the hollow cylindrical member 304 is located within the lumen of the second hollow cylindrical member 306. In this embodiment, the electrolysis wire 320 runs along the outer wall 904 of the hollow cylindrical member 306.

In another embodiment, shown in FIG. 9C, the electrolysis wire 320 extends within a lumen 326 used to inflate or expand the balloon. In another embodiment, shown in FIG. 9D, the electrolysis wire 320 is located within the wall of the catheter 300.

Figure 9E:
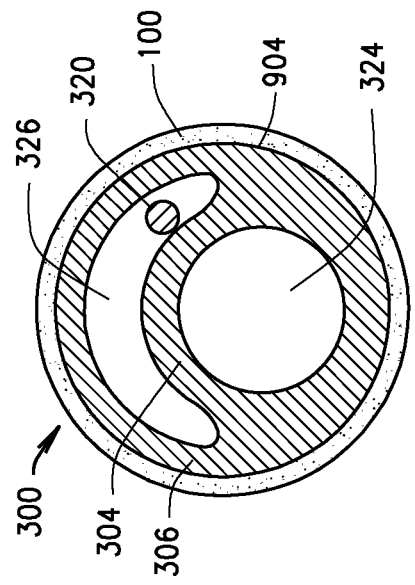
Figure 9D:
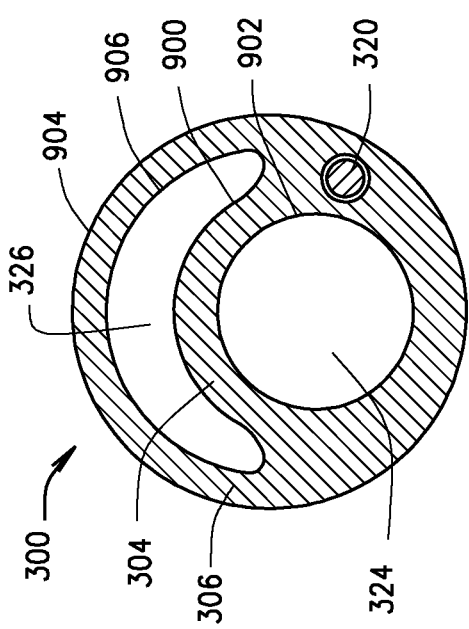

FIG. 9E depicts an axial cross-sectional view of the double lumen catheter 300 attached to the balloon 100. The balloon 100 is in fluid communication with 326 and is detached by the electrolysis wire 320 extending through the wall of the catheter 300.

Figure 10C:
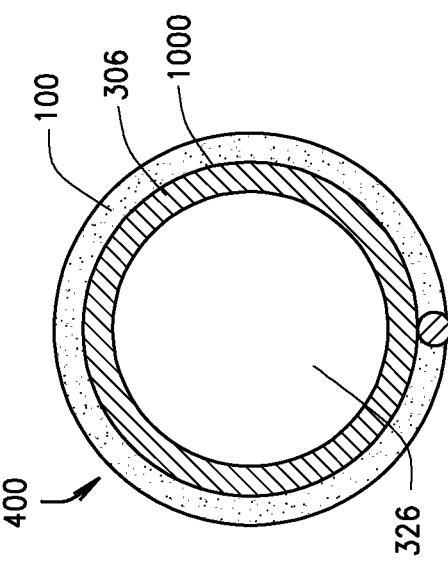
FIGS. 10A-C depict axial cross-sectional views of embodiments of the detachable balloon delivery device.
Figure 10B:
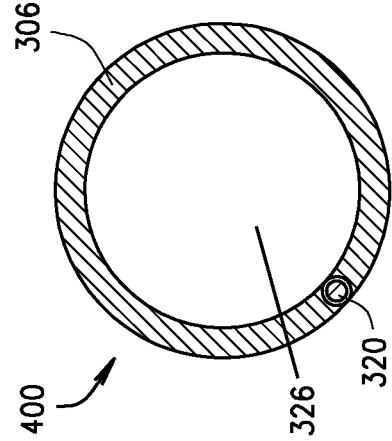
Figure 10A:
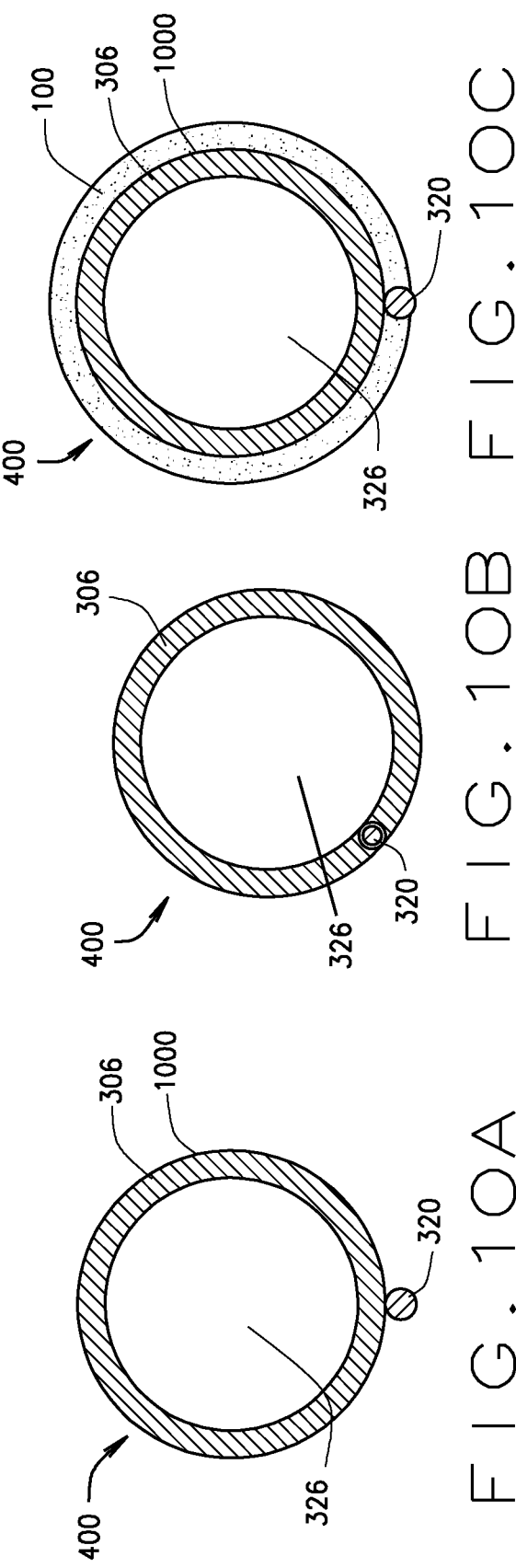

FIG. 10A is an axial cross-sectional view of the single lumen catheter 400. As shown, the electrolysis wire 320 runs along the outer wall 1000 of the hollow cylindrical member 306. In another embodiment, shown in FIG. 10B, the electrolysis wire 320 runs within the wall of the cylindrical member 306. FIG. 10C depicts an axial cross-sectional view of the single-lumen catheter 400 attached to the balloon 100. The balloon 100 is initially welded, soldered, or glued to the outer wall 1000 of the hollow cylindrical member 306 and is detached by the electrolysis wire 320 extending along the outer wall.

Figure 13A:
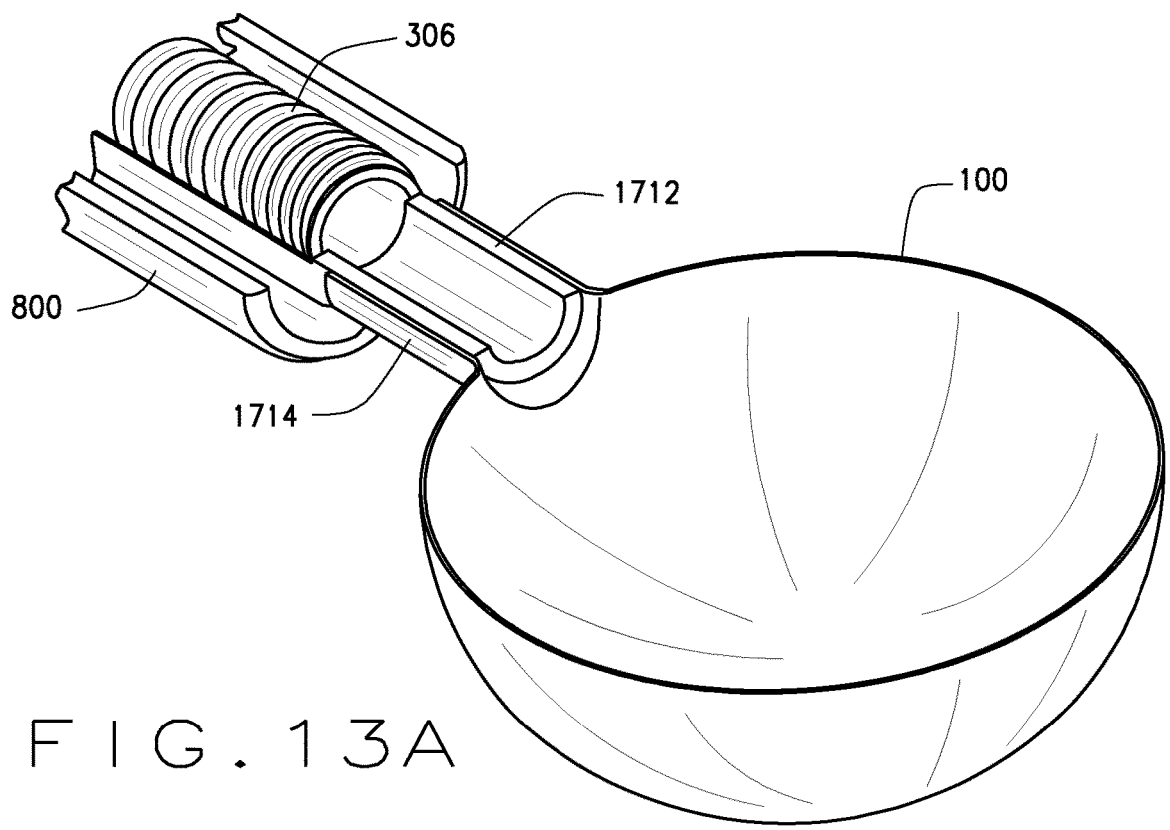
FIGS. 13A-B depict means for attaching a metal balloon to a delivery device.
Figure 13B:
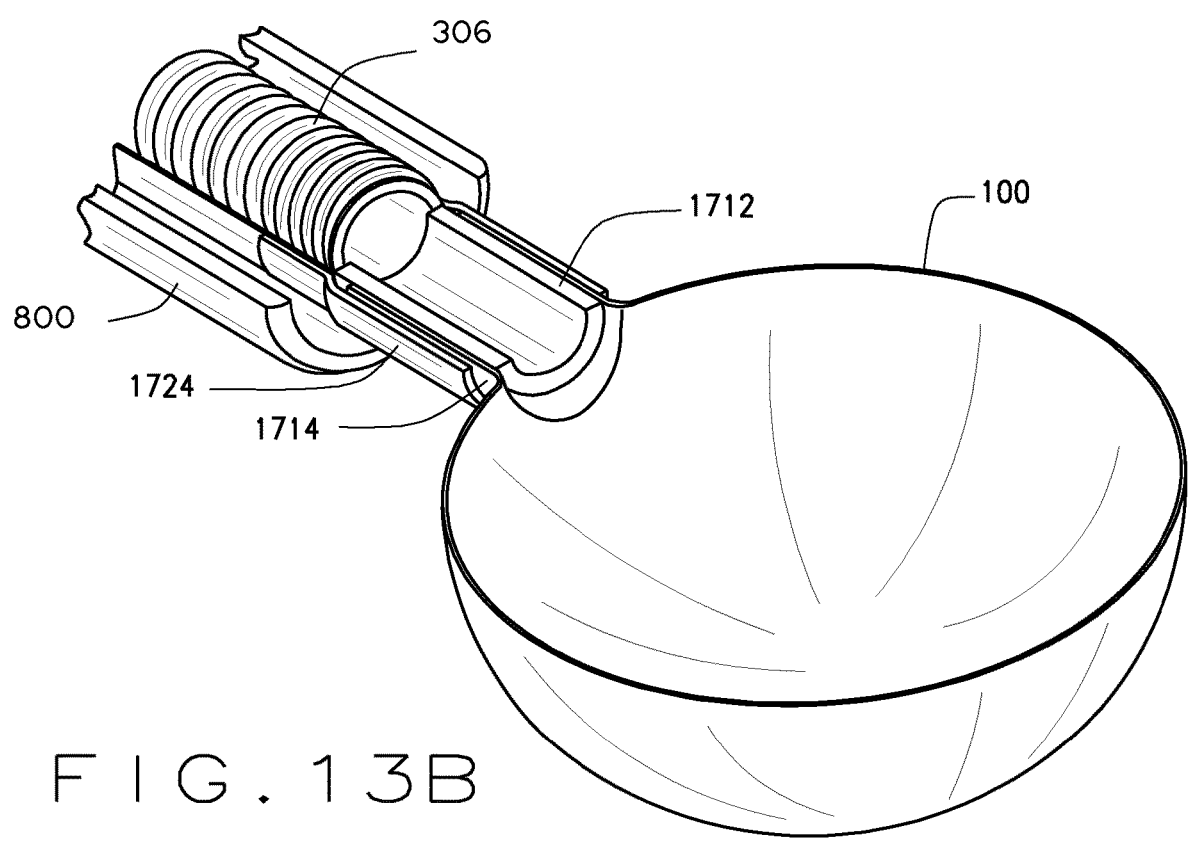

The balloon 100 may also engage to the delivery device through a frictional engagement, wherein the opening or neck of the balloon and the distal end of the delivery device are matched to fit together, but there is no bond (such as with adhesive or solder) between the balloon and the delivery device. Rather, the inflated balloon 100 and the delivery device are simply pulled apart. The balloon 100 may be detached from the delivery catheter by pulling the delivery catheter away from the balloon or by pushing the balloon away from the delivery catheter. FIGS. 13A-B depict embodiments of the medical device 500 wherein a friction fit is used to attach the balloon 100 and the delivery device. As shown in FIG. 13A, the neck 1714 of the balloon 100 is frictionally engaged on the outside of the distal end 1712 of the delivery device 306. For this example, the medical device 500 was passed through a guide catheter 800 with the balloon compressed, then the removable wire was withdrawn from the delivery device and the balloon 100 was inflated. In this example, the guide catheter 800 can then be advanced up to the wall of the inflated balloon 100, and then the delivery device can be pulled back or the guide catheter 800 can be pushed forward, to cause detachment of the inflated balloon. As shown in FIG. 13B, an elastic sleeve or wrap 1724 can be bonded to the delivery device 306 and then can frictionally engage the outside of the neck 1714 of the balloon 100, while the distal end of the delivery device 1712 simultaneously frictionally engages the inner surface of the neck 1714 of the balloon 100.

The balloon wherein the exterior surface of the balloon comprises a plurality of projections, that are either straight or branched, made of nitinol or fibers.

The balloon wherein the projections range in length from 0.01 µm to about 57 µm.

It will be appreciated that the device and method of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive and the scope of the invention is, therefore indicated by the appended claims rather than by the foregoing description. All changes which come within the meaning and range of equivalency of the claims are to be embraced within their scope.

What is claimed is:

1. A method of occluding a blood vessel, an aneurysm or other vascular abnormality, or a portion of a vascular system of a patient with a hollow structure comprising a gold continuous wall, the method comprising the steps of:
   positioning a guide wire at a desired location in the vascular system;
   advancing a medical device comprising a delivery catheter and the hollow structure over the guide wire, wherein the hollow structure is in a compressed configuration, and positioning the hollow structure in the compressed configuration at the desired location in the vascular system;
   removing the guide wire;
   expanding the hollow structure from the compressed configuration to an expanded configuration by injection of a fluid through an opening of the hollow structure and directly into a central void of the hollow structure to provide an expanded hollow structure;
   detaching the expanded hollow structure from the delivery catheter, leaving the expanded hollow structure at the desired location to occlude the desired location, wherein, no solid or semi-solid material, or support structure not derived from the patient, is required in the central void of the hollow structure to at least assist in causing the hollow structure to assume the expanded configuration or to remain fully expanded after detachment; and
   removing the delivery catheter.

2. The method of claim 1, wherein the guide wire is removed after detaching the expanded hollow structure from the delivery catheter.

3. The method of claim 1, wherein:
   the delivery catheter further comprises a first cylindrical member that defines a first lumen and a second cylindrical member that defines a second lumen;
   the delivery catheter is dimensioned to deliver the fluid from a fluid source at a proximal end of the delivery catheter through the first lumen defined by the first cylindrical member and into the central void of the hollow structure at a distal end of the delivery catheter; and
   wherein the delivery catheter is dimensioned to allow for passage of the guide wire through an entire length of the medical device through the second lumen defined by the second cylindrical member.

4. A method of occluding a blood vessel, an aneurysm or other vascular abnormality, or a portion of a vascular system of a patient with a hollow structure comprising a gold continuous wall, the method comprising the steps of:
   inserting a guide catheter into the vascular system;
   positioning the guide catheter at a desired location in an artery or a vein of the vascular system;
   advancing a medical device comprising a delivery catheter and the hollow structure through the guide catheter, wherein the hollow structure is in a compressed configuration, and positioning the hollow structure in the compressed configuration at the desired location in the vascular system;
   expanding the hollow structure from the compressed configuration to an expanded configuration by injection of a fluid through an opening and directly into a central void of the hollow structure to provide an expanded hollow structure;
   detaching the expanded hollow structure from the delivery catheter after the hollow structure is fully expanded, leaving the expanded hollow structure at the desired location to occlude the desired location, wherein, no solid or semi-solid material, or support structure not derived from the patient, is required in the central void of the hollow structure to at least assist in causing the hollow structure to assume the expanded configuration or to remain fully expanded after detachment; and
   removing the delivery catheter.

5. The method of claim 4, wherein:
   the delivery catheter further comprises a cylindrical member that defines a lumen; and
   wherein the delivery catheter is dimensioned to deliver the fluid from a fluid source at a proximal end of the delivery catheter through the lumen and into the central void of the hollow structure at a distal end of the delivery catheter.

6. The method of claim 1 or 4, wherein the hollow structure, when in the expanded configuration, assumes a generally cylindrical or generally rounded form comprising a single-lobed body defined by the wall with an interior surface, an exterior surface, and the opening, and wherein the interior surface of the wall defines the central void of the hollow structure, and wherein the opening in the wall allows for the injection of the fluid from the delivery catheter into the central void of the hollow structure.

7. The method of claim 1 or 4, wherein the hollow structure has a wall thickness ranging from 5 µm to 20 µm.

8. The method of claim 1 or 4, wherein, when the hollow structure is in the expanded configuration, the expanded hollow structure has an expanded diameter ranging from 2 mm to 30 mm.

9. The method of claim 1 or 4, wherein the expanded hollow structure has a length of between 5 mm to 60 mm.

10. The method of claim 1 or 4, wherein an exterior surface of the expanded hollow structure further comprises microscopic projections.

11. The method of claim 10, wherein the projections range in length from 0.01 µm and to 57 µm.

12. The method of claim 1 or 4, further comprising coupling the hollow structure to the delivery catheter by friction, without an adhesive bond, solder, or weld.

13. The method of claim 12, wherein detaching the delivery catheter from the expanded hollow structure further comprises pulling the delivery catheter away from the expanded hollow structure.

14. The method of claim 12, wherein the expanded hollow structure and the delivery catheter are pulled apart by withdrawing the delivery catheter while the expanded hollow structure is held in place.

15. The method of claim 1 or 4, further comprising:
incorporating a radiopaque marker band or spot into the medical device; and,
identifying a location where separation of the hollow structure and the delivery catheter is to occur.

16. The method of claim 15, further comprising identifying a distal end of the delivery catheter with the radiopaque marker band or spot.

17. The method of claim 1 or 4, wherein, when the hollow structure is in the compressed configuration prior to expansion, the hollow structure has a compressed diameter ranging from 2-5 Fr.

18. The method of claim 1, 4, 3, or 5, wherein the hollow structure comprises a body and a proximal neck that projects away from the body, and wherein the proximal neck is configured to fit around a distal end of the delivery catheter, forming a friction fit.

19. The method of claim 18, wherein the friction fit is increased by an elastic sleeve or wrap that holds the proximal neck and the delivery catheter together.

20. The method of claim 19, wherein detaching the delivery catheter from the expanded hollow structure further comprises pulling the delivery catheter away from the expanded hollow structure.

21. The method of claim 19, wherein the expanded hollow structure and the delivery catheter are pulled apart by withdrawing the delivery catheter while the expanded hollow structure is held in place.

22. The method of claim 18, wherein detaching the delivery catheter from the expanded hollow structure further comprises pulling the delivery catheter away from the expanded hollow structure.

23. The method of claim 18, wherein the expanded hollow structure and the delivery catheter are pulled apart by withdrawing the delivery catheter while the expanded hollow structure is held in place.

24. The method of claim 1 or 4, wherein detaching the delivery catheter from the expanded hollow structure further comprises pulling the delivery catheter away from the expanded hollow structure.

25. The method of claim 1 or 4, wherein the expanded hollow structure and the delivery catheter are pulled apart by withdrawing the delivery catheter while the expanded hollow structure is held in place.

26. The method of claim 1 or 4, wherein the hollow structure further comprises a body and a proximal neck that projects away from the body and is joined to the delivery catheter by an adhesive or glue.

27. The method of claim 26, wherein an insulated conductor wire for transmitting an electrical current extends from at least a proximal end of the delivery catheter to at least a distal end of the delivery catheter along a longitudinal axis of the delivery catheter, the method further comprising:
when the hollow structure is expanded in a human patient, passing electricity through the conductor wire; and
dissolving a portion of the proximal neck of the hollow structure.

28. The method of claim 27, wherein the electrical current is a DC current.

29. The method of claim 27, wherein the portion of the proximal neck of the hollow structure that is dissolved comprises a strip of exposed conductive material.

30. The method of claim 29, wherein the strip of exposed conductive material is produced by etching or ablation.

31. The method of claim 30, wherein the etching or ablation is made by a laser.

32. The method of claim 27, wherein the insulated conductor wire is embedded within the wall of the delivery catheter.

33. The method of claim 1 or 4, further comprising contacting an inner surface of the blood vessel or portion of the vascular system with at least 50% of an exterior surface of the hollow structure, after expansion and detachment.

34. The method of claim 1 or 4, further comprising filling at least 50% of a lumen of the aneurysm with the expanded hollow structure, after expansion and detachment.

35. The method of claim 1 or 4, wherein the hollow structure comprises a proximal neck and a distal neck, and the method further comprising closing and sealing of one of the proximal neck and the distal neck after separation from the delivery catheter, wherein pressure inside the central void of the expanded hollow structure is not higher than the pressure outside the expanded hollow structure after detachment.

36. The method of claim 35, wherein, after separation from the delivery catheter, one of the proximal neck or the distal neck is sealed and one of the proximal neck or the distal neck remains open.

37. The method of claim 1 or 4, further comprising changing the shape of the expanded hollow structure by the application of an external force.

38. The method of claim 37, wherein the application of the external force occurs before detachment.

39. The method of claim 38, further comprising applying the external force using an angioplasty balloon.

40. The method of claim 37, wherein the application of the external force occurs after detachment.

41. The method claim 40, further comprising applying the external force using an angioplasty balloon.

42. The method of claim 1 or 4, wherein at least one other expanded hollow structure is placed at the desired location of the vascular system.

43. The method of claim 1 or 4, wherein the blood vessel is an artery or vein.

44. The method of claim 1 or 4, wherein the aneurysm is a saccular aneurysm.

45. The method of claim 1 or 4, wherein the hollow structure further comprises a polymer layer or coating.

46. The method of claim 45, wherein a thickness of the polymer layer or coating is between 0.5 μm and 59 μm.

47. The method of claim 46, wherein a total thickness of the wall is between 3 82 m and 60 μm.

48. The method of claim 45, wherein a total thickness of the wall is between 3 μm and 60 μm.

49. The method of claim 45, wherein the polymer layer or coating is external to a gold layer.

50. The method of claim 45, wherein the polymer layer or coating is internal to a gold layer.

51. The method of claim 45 wherein the polymer layer or coating is configured to reduce leaking of the fluid from the hollow structure during expansion.

52. The method of claim 45 wherein the polymer layer or coating is a continuous layer.

53. The method of claim 1 or 4, wherein at least a portion of a catheter wall of the delivery catheter is reinforced with wound or braided wire.

54. The method of claim 53, wherein the wire is comprised of stainless steel or nitinol.

55. The method of claim 1 or 4, wherein a length of the delivery catheter is 75-225 cm.

56. The method of claim 1 or 4, wherein at least a portion of the wall of the hollow structure is formed by electroforming.

57. The method of claim 1 or 4, wherein an exterior layer of the hollow structure is formed by different methods than an interior layer or coating.

58. The method of claim 1 or 4, wherein the hollow structure comprises an outer layer comprising gold and an inner layer comprising a polymer, and wherein the gold layer and the polymer layer are bonded together.

59. The method of claim 1 or 4, further comprising annealing the hollow structure.

60. The method of claim 1 or 4, further comprising folding the hollow structure to form one or more pleats.

61. The method of claim 60, further comprising compressing the one or more pleats against a portion of the delivery catheter.

62. The method of claim 1 or 4, wherein the fluid comprises water, saline or radiographic contrast.

63. The method of claim 62, wherein the fluid is injected at a pressure less than 5 atmospheres.

64. The method of claim 1 or 4, wherein the fluid is injected at a pressure less than 5 atmospheres.

* * * * *